United States Patent [19]
Lee et al.

[11] Patent Number: 6,057,150
[45] Date of Patent: May 2, 2000

[54] BIAXIAL STRAIN SYSTEM FOR CULTURED CELLS

[75] Inventors: Ann A. Lee, San Clemente; Jessie Carolyn Laib, Pinole, both of Calif.

[73] Assignee: Bio-Rad Laboratories, Inc., Hercules, Calif.

[21] Appl. No.: 09/156,769

[22] Filed: Sep. 18, 1998

Related U.S. Application Data

[60] Provisional application No. 60/059,396, Sep. 19, 1997.

[51] Int. Cl.$^7$ .................................................. C12M 3/04
[52] U.S. Cl. .................... 435/288.3; 435/288.4; 435/305.1; 435/305.2; 435/297.5
[58] Field of Search ............................. 435/288.3, 288.4, 435/297.5, 305.1, 305.4; 29/DIG. 42; 425/DIG. 53; 38/102, 102.1, 102.2, 102.3, 102.4, 102.6, 102.8; 69/19.1–19.3; 73/788, 826, 38, 40

[56] References Cited

U.S. PATENT DOCUMENTS

| | | |
|---|---|---|
| 173,720 | 2/1876 | Guerin . |
| 3,422,669 | 1/1969 | Craft . |
| 4,357,869 | 11/1982 | Wadstein . |
| 4,839,280 | 6/1989 | Banes . |
| 4,851,354 | 7/1989 | Winston et al. . |
| 5,073,482 | 12/1991 | Goldstein . |
| 5,153,136 | 10/1992 | Vandenburgh . |
| 5,348,879 | 9/1994 | Shaprio et al. . |
| 5,406,853 | 4/1995 | Lintilhac et al. . |
| 5,451,524 | 9/1995 | Coble et al. . |
| 5,686,303 | 11/1997 | Korman . |

OTHER PUBLICATIONS

N. Caille et al. *Annals of Biomedical Engineering* (1998) 26: 409–416.
J.A. Gilbert et al. *J. Biomech.* (Sep. 1994) 27(9): 1169–77.
S.R.P. Gudi et al. *Am. J. Physiol.* 274: (*Cell Physiol.*43:) (1998) C1424–1428.
C.T. Hung et al. *J. Biomechanics* (1994) 27(2): 227–232.
A.A. Lee et al. *Am J. Physiol.*271 (Cell Physiol. 40) (1996) C1400–C1408.
M. Liu et al. *Am. J. Physiol.* 263 (*Lung Cell. Mol. Physiol.* 7)  (1992) L376–L383.
D.A. MacKenna et al. *J. Clin. Invest.* (Jan. 1998) 101(2): 301–310.
J.L. Schaffer et al. *Journal of Orthopaedic Research* (1994) 12: 709–719.
M. Sotoudeh et al. *Annals of Biomedical Engineering*(1998) 26: 1–9.
J.L. Williams et al. *Journal of Biomechanical Engineering* (Aug. 1992) 114: 377–384.
F.K. Winston et al. *J. Applied Physiol.* (1989) 67(1): 397–405.
"New Products Information Packet," Flexcell International Corp., McKeesport, PA (no date provided).

*Primary Examiner*—William H. Beisner
*Attorney, Agent, or Firm*—Townsend and Townsend and Crew LLP

[57] ABSTRACT

Biological cells plated on an elastic membrane are placed under biaxial strain for purposes of observation by a device that includes a support with an opening over which the membrane is secured, a movable cylinder coaxial with the opening and fitting closely but movably within the opening, and an actuating member that stabilizes and controls the position of the cylinder relative to the opening. The actuating member is coupled to the support by a threaded connection while engaging the movable cylinder. The degree of membrane stretch is accurately controlled by the rotation of the actuating member.

14 Claims, 16 Drawing Sheets

BIAXIAL STRAIN SYSTEM FOR CULTURED CELLS

CROSS REFERENCE TO RELATED APPLICATION

This application is based on provisional patent application No. 60/059,396, filed in the United States Patent and Trademark Office on Sep. 19, 1997, and hereby claims all benefits that are legally served thereby. The entire contents of provisional patent application No. 60/059,396 are incorporated herein by reference.

BACKGROUND OF THE INVENTION

1. Field of the Invention

This invention relates to laboratory procedures for studying biological cells that have been physically deformed by mechanical stretching.

2. Description of the Prior Art

During the everyday physical activity of the human body, cells from tissues such as skeletal muscles, smooth muscles, and heart muscles are subjected to physical loads that cause the cells to stretch up to 10% or more. It is well established that mechanical stretch can have significant effects on cellular function, such as stimulation of intracellular $Ca^{2+}$ release, increased gene expression, or release of paracrine growth factors. Published literature describing mechanical cell stretch and its effects on cellular function include papers by Perrone, C. E., et al., *J. Biol. Chem.* 270:2099–2106 (1995), Sadoshima, J., et al., *Cell* 75:977–984 (1993), and Wilson, E., et al., *J. Clin. Invest.* 96: 2364–2372 (1995). The effects of cell stretching are typically studied by growing the cells on a flexible membrane serving as a cell culture substrate, then deforming the membrane and, while maintaining the deformation, performing any of various procedures on the cells to study aspects of their biological function.

The literature reports the deformation of membranes in various ways for purposes of studying the effect on cell functions. Applying a uniaxial stretch is one example. Studies of cell and molecular responses to static and cyclic mechanical loading under uniaxial stretch are reported by Sadoshima, J., et al., cited above, Simpson, D. G., et al.,*Ann. NY Acad. Sci.* 752:131–140 (1995), and Vandenburgh, H. H., *Am. J. Physiol.* 262 (*Regulatory Integrative Comp. Physiol.* 31):R350–R355 (1992). While the force in a uniaxial stretch is applied in a single direction, the resulting deformation of the substrate is actually a specific type of biaxial strain, since in addition to the stretching strain a compressive strain also occurs in directions transverse to the axis of the applied load, as reported by Hung, C. T., et al., *J. Biomech.* 27:227–232 (1994). Moreover, the strain distribution is nonhomogeneous, and significant shears are present near the clamped edges of the substrate. Thus, the result is a strain whose components and directions are not controlled and not fully quantified.

The literature also reports membrane deformation by biaxial stretch. Non-planar deformations, for example, have been used for achieving biaxial stretch. This is done by fixing the cells on a flexible circular substrate which is clamped to a holder, and applying a pressure differential across the substrate. The pressure differential inflates the substrate, causing it to bulge. As reported by Gilbert, J. A., et al., *J. Biomech.* 27:1169–1177 (1994), the strains produced in this type of device are nonhomogeneous in distribution, ranging in some cases between 0 and 30% over the surface of the substrate. Furthermore, the stretch differs from one axis to the next and shears may be present. These differences produce variations associated with the orientations of randomly plated polar cells, as well as variations in cellular responses. Also, focal plane differences in the substrate and the working distance requirements of an inverted microscope objective make it impractical to view cells that cultured on substrates that are inflated (caused to bulge) in this manner.

A further disadvantage of both uniaxial deformation and non-planar indentation is that the states of deformation that occur in these methods are not accurately defined. In addition, the substrate deformation is nonhomogeneous, and there is a lack of control over the type and magnitude of the strain imposed by the stretch. Quantifying cell deformation is essential for a complete understanding of the relationships between mechanical loads and cell function, in the same way that quantitative testing and theoretical analysis have been necessary for identifying relationships between structure and mechanical function in tissues and cells.

Biaxial stretch in a planar configuration can be achieved by pressing an object such as an indentation ring against the membrane surface. Devices operating in this manner are disclosed by Hung, C. T., et al., *J. Biomech.* 27:227–232 (1994) and by Schaffer, J. L., et al., *J. Orthopaedic Res.* 12:702–719 (1994). In these devices, the indentation ring and a stationary ring are pressed against opposite sides of the membrane, and in Hung et al., the indentation ring is the larger of the two. The circle of contact between the indentation ring and the membrane thus lies outside that of the stationary ring. The indentation ring is generally located below the membrane, and the stretch is controlled by pressing the indentation ring upward against the area of the membrane surrounding the stationary ring, consequently increasing the stretch across the stationary ring. The flat portion of the membrane that is stretched across the smaller stationary ring thus remains coplanar, but the larger movable indentation ring interferes with the access to the membrane by a microscope, particularly an inverted microscope. This precludes visualization of cells at high strains (i.e., strains of 1% or more).

SUMMARY OF THE INVENTION

The present invention resides in a novel apparatus for producing planar biaxial stretch in a membrane which avoids the problems of planar biaxial stretch devices of the prior art. In the present invention, both the stationary ring (to which the membrane is affixed) and the indentation ring are on the same side of the membrane, with the indentation ring smaller than (and inside) the stationary ring. Thus, when the indentation ring is pressed against the membrane to apply a biaxial stretch, the stretched portion of the membrane spans the rim of the indentation ring itself in a planar configuration. In relation to the moving and functional parts of the device (i.e., those parts other than the stand on which the other parts rest), the membrane always forms the lowest plane of the device. This permits one to place the device on a stand above an inverted microscope and to maintain the membrane at a fixed vertical position relative to the stand at all degrees of stretching.

The biaxial stretching device of this invention includes (i) a support with a tubular passage whose lower end is an opening over which the membrane is secured, (ii) a movable cylinder coaxial with the opening and fitting closely but movably within the opening, and (iii) an actuating member that stabilizes and controls the position of the cylinder inside the tubular passage and relative to the opening. The actuating member is coupled to the membrane support through a threaded connection and engages the cylinder, so that rotation of the actuating member along the threaded connection varies the position of the cylinder relative to the membrane support. The edge of the cylinder thus protrudes through the opening to press against and thereby stretch the membrane, and the distance of protrusion and hence the degree of stretch vary with the degree or angle of rotation of the actuating member relative to the support. During stretching, the entire area of the membrane that stretches across the rim of the cylinder remains planar, and the rim of the cylinder and hence the membrane form the lowermost plane of the device, exclusive of any stand that these parts may rest on.

The strain is distributed along the area spanning the opening of the tubular passage where the movable cylinder presses against the membrane. By varying the pitch of the threads, the device can be constructed to achieve any degree of sensitivity in selecting or varying the applied strain. The device applies the strain while retaining the flatness of the membrane, which facilitates observation of the stretched cells and the use of sophisticated imaging or microscopy. The threaded surfaces of the membrane support and the movable cylinder may be circular in profile, and the movable cylinder and tubular passage may also have circular cross sections, in which case the biaxial strain will be evenly and uniformly distributed across the area spanning the protruding edge of the cylinder. Alternatively, the movable cylinder, and optionally the tubular passage as well, may have profiles that are other than circular, for example elliptical or any other closed curve to achieve any of numerous variations on biaxial stretches. An elliptical profile will produce a biaxial strain with differing values along the two orthogonal axes of the ellipse. The terms "cylinder" and "cylindrical" are used herein to denote any surface formed by moving a straight line parallel to a fixed straight line and intersecting a fixed planar closed curve. The cross section may thus be circular, elliptical, or any other closed curve. Circular and elliptical cross sections are preferred, as illustrated and explained below.

This invention also encompasses multiple-membrane devices in which the membrane support contains two or more tubular passageways and cylinders of complementary shape to fit inside the passageways, rather than just one passageway and cylinder. With structures of this type, several membranes can be stretched individually, one secured over the bottom opening of each tubular passageway. The stretching component of these devices is a plurality of cylinders, equal in number to, and spaced in an array complementary to, the tubular passageways. A single actuating member, which is coupled to the support by a threaded connection as in the single-membrane device, engages the all of the cylinders and controls their position and movement simultaneously.

A primary advantage of this invention in each of its embodiments is that it facilitates the visualization of the cells in a focused plane during the stretch by an inverted microscope. This allows cell strains and morphology to be measured and tracked in a highly precise manner in real time. The device maintains this precision and control through a wide range of biaxial strain values to an elastic substrate and thus to cultured cells plated on the substrate.

These and other features and advantages of the invention and the manner in which they are achieved are explained in detail below.

DETAILED DESCRIPTION OF THE INVENTION AND PREFERRED EMBODIMENTS

Figure 4:
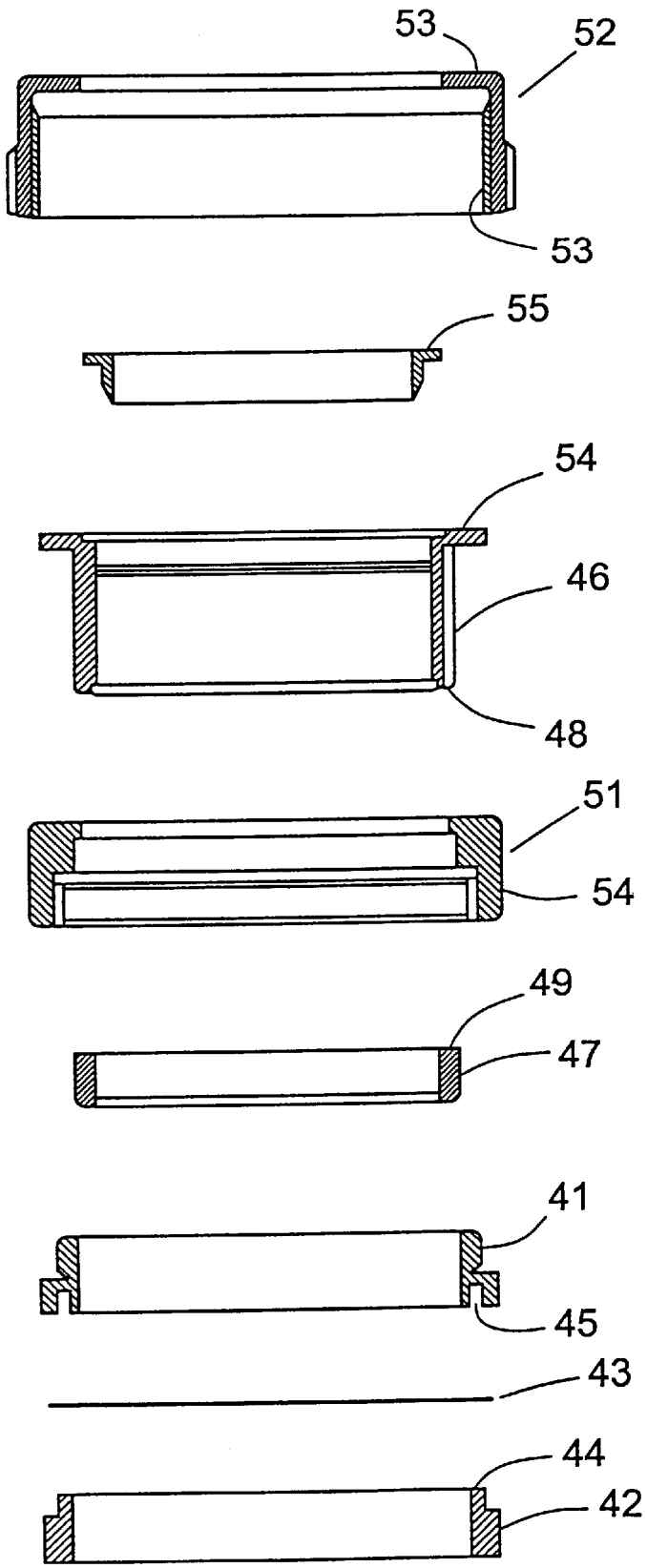
FIG. 4 is an exploded vertical cross section view of a multiwell equibiaxial stretch device in accordance with the present invention.
Figure 5:
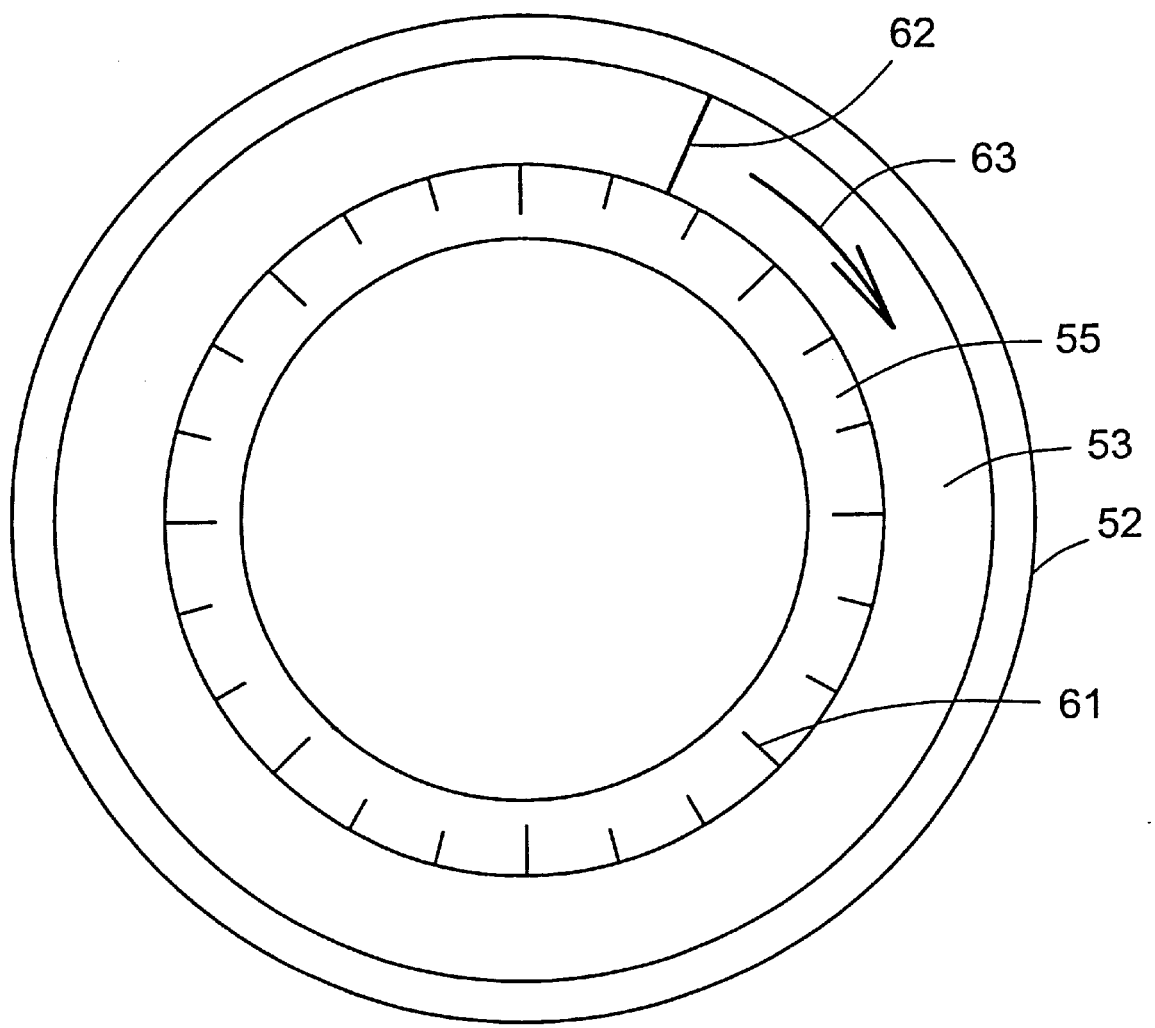
FIG. 5 is an exploded cross section view of another single-well equibiaxial stretch device in accordance with the invention.
Figure 6:
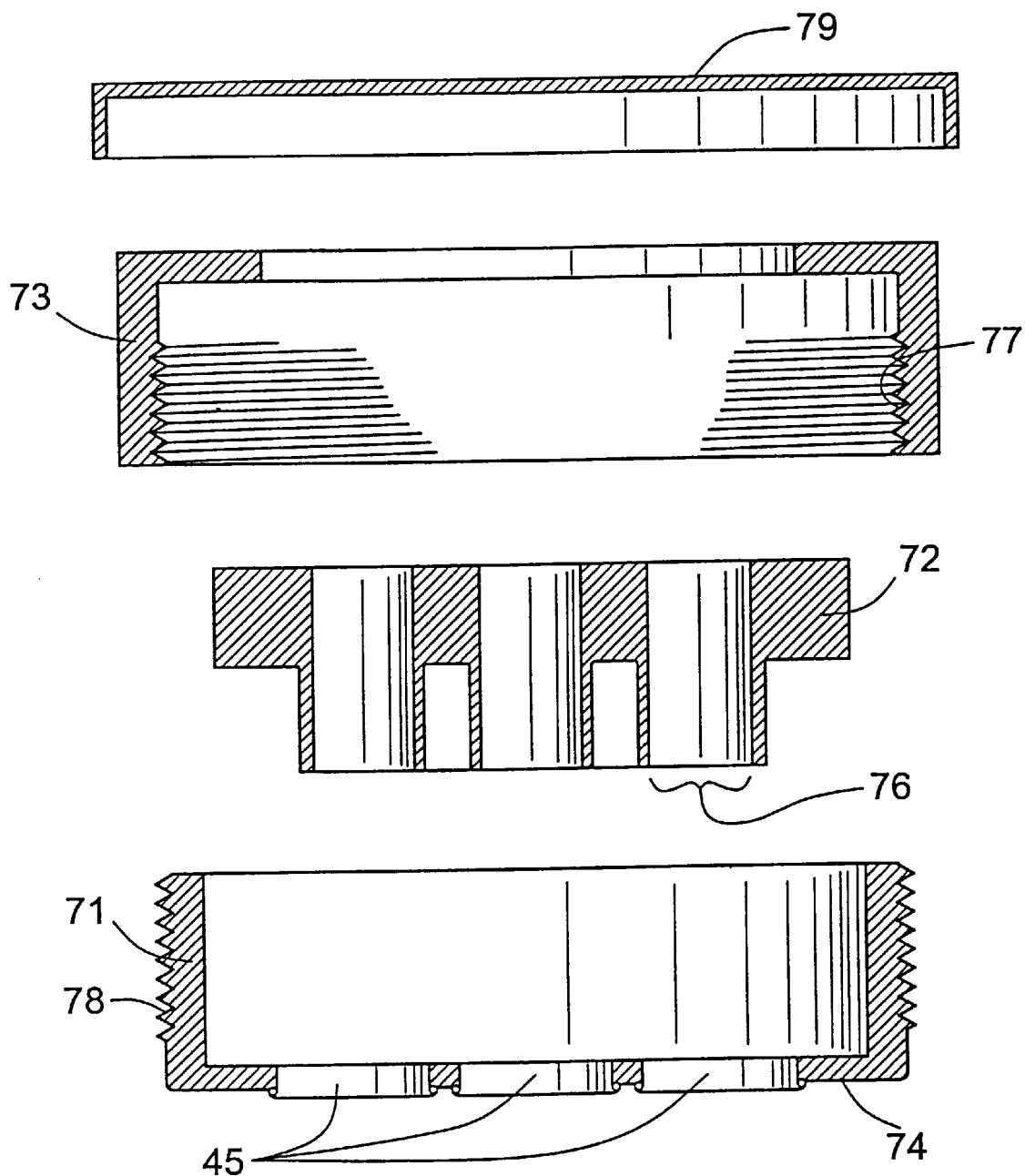
FIG. 6 is a top view of two of the components of the device of FIG. 5.

Within the limitations set forth above, this invention can be implemented in a variety of structures and embodiments. To promote an understanding of the features that define the novelty of the invention, however, a few specific examples of equibiaxial cell stretch devices within the scope of the invention are explained herein in detail. These devices are shown in the attached figures—single-well devices for stretching and observing a single membrane to which cells have been plated (FIGS. 1, 2 and 3) and a multiwell device for simultaneously stretching and observing two or more such membranes (FIGS. 4, 5, and 6).

Figure 1:
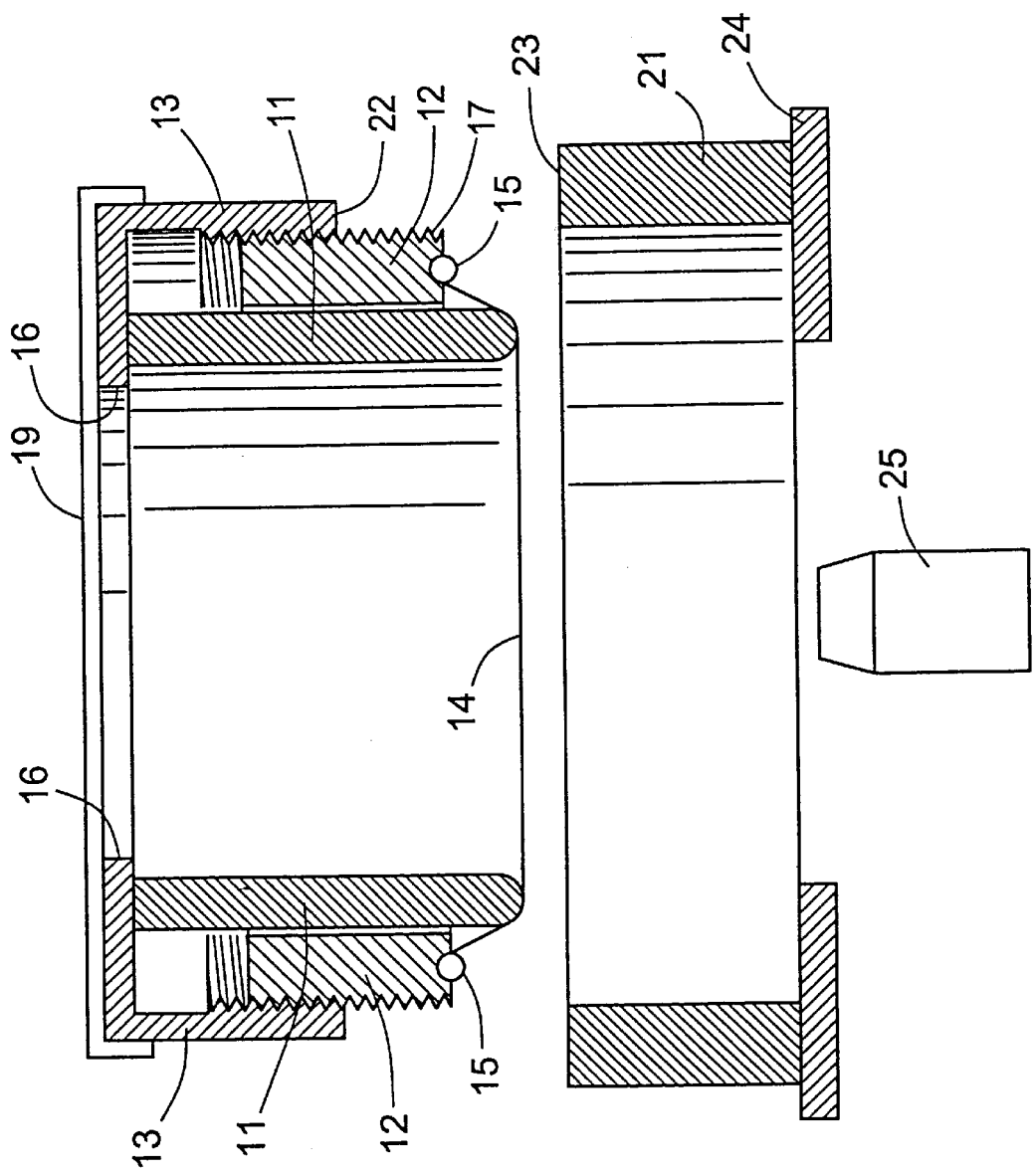
FIG. 1 is a vertical cross section of a single-well equibiaxial stretch device in accordance with the present invention.
Figure 2:
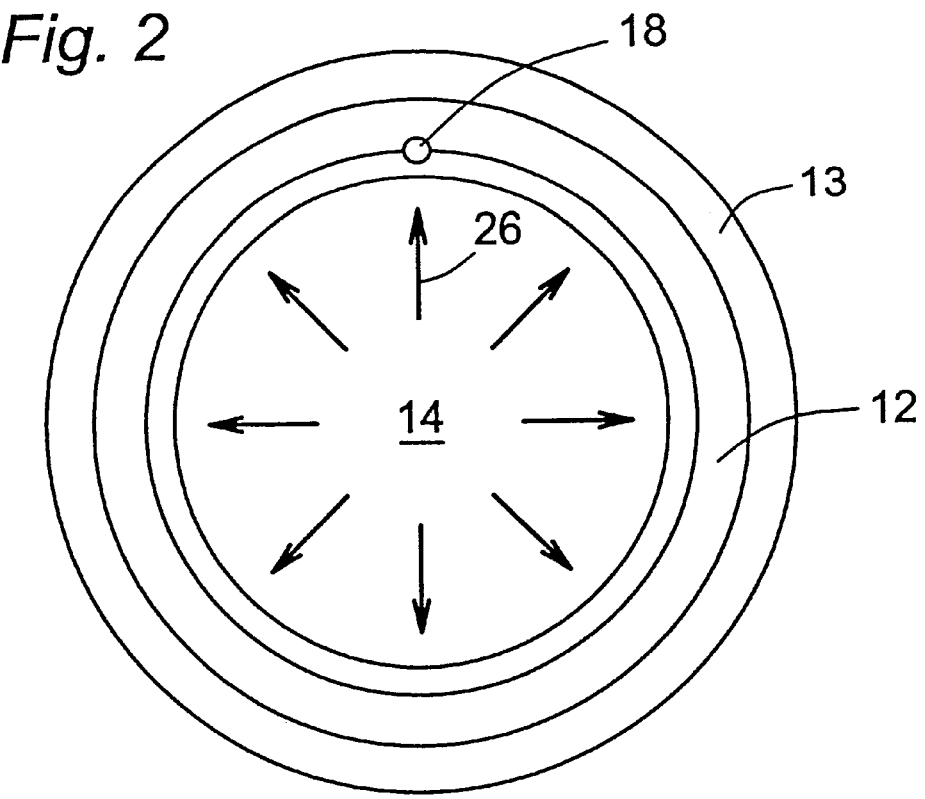
FIG. 2 is a horizontal cross section of the device of FIG. 1.

The single-well device of FIGS. 1 and 2 contains three concentric cylinders—an inner cylinder 11 serving as the stretching component, an intermediate cylinder 12 serving as the membrane support, and an outer cylinder 13 serving as the actuating member. All three cylinders are hollow circular cylinders, open at both ends. The cell substrate 14, which can for example be a transparent silicone elastic membrane, is secured to the bottom of the intermediate cylinder 12 spanning the circular opening at the base of the cylinder. A typical membrane is 0.1 to 0.25 mm in thickness, and is a gloss-finish silicone elastic membrane, obtainable from Specialty Manufacturing, Saginaw, Mich., USA.

The membrane 14 is attached to the intermediate cylinder by any conventional means that will hold the membrane in place while stress is applied to stretch the membrane. In the particular embodiment shown in FIGS. 1 and 2, the membrane is secured by means of a silicone rubber O-ring 15 (such as for example product no. 2–232 of ASI Marine and Industrial, San Diego, Calif., USA). The O-ring 15 fits tightly in a circular groove along the bottom edge of the cylinder, pressing the membrane in the groove. The inner (stretcher) cylinder 11 fits inside the membrane support cylinder 12 in a snug fit which permits the stretcher cylinder to move relative to the support cylinder, the movement being primarily, if not entirely, in the axial direction.

The outer (actuating) cylinder 13 encircles the membrane support cylinder, and has an inwardly directed shoulder or flange 16 that extends over the edges of both the inner (stretching) and intermediate (membrane support) cylinders. The outer (actuating) cylinder 13 and the intermediate (membrane support) cylinder 12 are coupled by a thread (screw) connection 17 formed by outward-facing threads on the intermediate cylinder mated with inward-facing threads on the outer cylinder. The intermediate (stretching) cylinder is thus compressed between the membrane 14 at the bottom and the flange 16 of the outer cylinder at the top. Rotation of the outer cylinder along the thread connection in an appropriate direction will raise the intermediate (membrane support) cylinder 12 relative to the inner (stretcher) cylinder 11. This will displace the peripheral edges of the membrane 14 further from the rim of the stretching cylinder 11, and the membrane will stretch in the direction shown by the arrows 26 (FIG. 2), producing a homogeneous, planar equibiaxial stretch.

Returning to FIG. 1, a membrane that is mounted across the bottom of the membrane support cylinder 12 is stretched by a technician holding the membrane support cylinder by the exposed threads 17 in one hand and turning the actuating cylinder 13 with the other hand. The amount of stretch is selected to a high degree of accuracy by the amount by which the actuating cylinder is turned. Once the selected stretch is achieved, the technician then places the three cylinders on a stand 21 which in this embodiment is simply a ring or short cylinder whose inner diameter is large enough to receive the portion of the intermediate cylinder 12 that extends below the actuating cylinder 13. The height of the stand 21 is great enough that the lower edge 22 of the actuating cylinder 13 can rest on the upper edge 23 of the stand, while leaving the membrane 14 suspended inside the stand, a short distance above the base of the stand. The stand 21 itself rests on a microscope stage 24 above an inverted objective lens 25. The stretched planar portion of the membrane 14 occupies the lowest horizontal plane of the three movable cylinders 11, 12, 13, and its height relative to the microscope stage 24 and objective lens 25 does not vary, regardless of the relative positions of the membrane support cylinder 12 and the stretcher cylinder 11 and hence regardless of the degree of stretch.

In a variation of the stand, not shown in the drawing, the stand may have three vertical fingers extending upward from a base, and the threaded area on the outside of the membrane support cylinder 12 may have three correspondingly located areas that are flattened or indented (and thread-free). The fingers will then reside against the thread-free areas and the operator can hold the stand stationary while rotating the actuating cylinder.

Returning to FIG. 1, the lower edge of the stretcher cylinder 11 (i.e., where the stretcher cylinder contacts the membrane 14) can have a smooth rounded profile to reduce friction at the membrane surface as the membrane is being stretched. A pin 18 is inserted between the stretcher cylinder 11 and the membrane support cylinder 12, the pin fitting inside opposing grooves on the facing surfaces of these cylinders to prevent rotation of the stretcher cylinder 11 as the actuating cylinder 13 is rotated. This prevents shearing movements of the membrane. The pin can be replaced by a protruding ridge in one of the two cylinders that fits inside a groove in the other cylinder. Friction can be further reduced by applying a nontoxic lubricant to all contacting parts of the device. In addition, the membrane (particularly silicone membranes) can be coated with extracellular matrix proteins to promote cell attachment and growth. Examples of such proteins are collagen, fibronectin, vitronectin, and laminin. A solution of 0.01% collagen type I (Sigma Chemical, St. Louis, Mo., USA) in 0.1 M acetic acid, for example, can be applied to the membrane by airbrushing (using a Badger Air-Brush, Franklin Park, Ill., USA). Alternatively, collagen as an 0.01% in phosphate-buffered saline (PBS) can be applied to the membrane by passive adsorption overnight at 25° C.

A lid 19, which can be for example a standard tissue culture dish, is placed over the outer (actuating) cylinder for protection of the device and its contents. The lid is preferably transparent to allow sterile visualization under a microscope. The actuating cylinder 13 may have grooved channels (not shown) to permit gas to enter or escape from the interiors of the cylinders while the lid is in place, thereby assuring that the pressures on both sides of the membrane 14 are equal, and facilitating gas exchange where necessary (for example, in an incubator or a controlled humidity environment).

Figure 3:
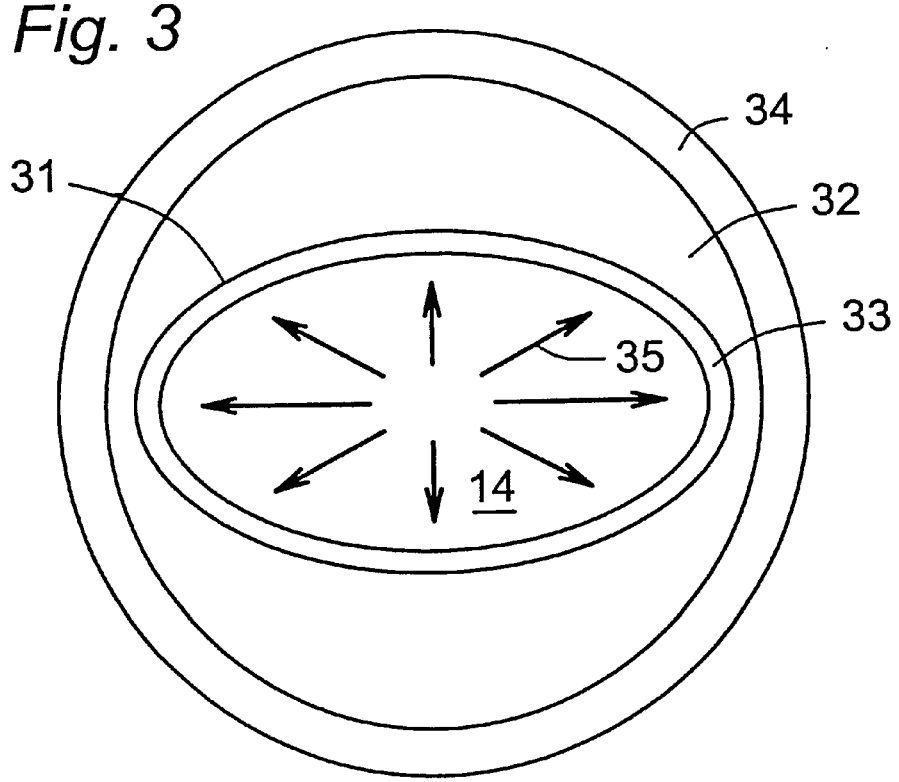
FIG. 3 is a horizontal cross section of a device which is a variation of the device of FIG. 1.

FIG. 3 shows a variation of the device of FIGS. 1 and 2, in a view corresponding to that of FIG. 2. The tubular passageway 31 in the membrane support cylinder 32 and the stretcher cylinder 33 in this variation are elliptical in cross section rather than circular. The O-ring (not shown) is likewise elliptical. The outer surface of the membrane support cylinder 32 and the inner surface of the actuating cylinder 34 are circular in cross section to permit a threaded connection between them. The stretcher cylinder 33 is actuated in the same manner as the stretcher cylinder 11 of FIGS. 1 and 2, but the resulting stretch is as indicated by the arrows 35, whose length (denoting the degree of stretch) varies with their location around the ellipse.

FIG. 4 shows an alternative construction for a single-well stretch device in accordance with the invention, with all parts shown in an exploded view. In place of the membrane support 12 and O-ring 15 of FIG. 1, the device of FIG. 4 has a membrane holder 41 and a snap ring 42 which hold the membrane 43 between them. A thin axial rim 44 at the top of the snap ring 42 mates with a circular channel 45 in the bottom of the membrane holder in a friction fit, pressing the peripheral edge of the membrane 43 into the channel. In place of the stretcher cylinder 11 of FIG. 1 is a pair of rings, upper 46 and lower 47. The contacting ends of these two rings are shaped such that the lower rim 48 of the upper ring has a curved profile to fit within a complementary curved indentation in the upper rim 49 of the lower ring. The lower ring 47 is the portion that contacts the membrane during the stretching, and can be made to be a disposable part, while the upper ring 46 can be made to be reusable.

The membrane holder 41 is threaded into a central ring that constitutes the body 51 of the device. The two parts 46, 47 of the stretcher component pass through the body 51 and the membrane holder 41 to stretch the ring. In place of both the actuating cylinder 13 and the lid 19 of FIG. 1 is a cap 52 in the form of a cylinder with threads 53 on its internal surface that mate with threads on the outer surface 54 of the body 51. The cap 52 has an inwardly directed flange 53 that engages an outwardly directed flange 54 on the upper ring 46 section of the stretcher. Thus, by rotating the cap 52 and screwing it down over the threads of the body 51, the stretcher rings 46, 47 are advanced downward relative to the body 51 and membrane holder 41, and the membrane 43 is stretched. To facilitate the turning of the cap 52, the parts can be constructed of a self-lubricating or low-friction material such as DELRIN®, a thermoplastic acetal resin (E. I. DuPont de Nemours & Co., Wilmington, Del., USA), and threads with a rounded profile can be used. As in FIG. 1, the parts are constructed so that when the cap 52 is rotated, the body 51 holds all other parts stationary.

To calibrate and quantify the degree of stretch and to stretch membranes in a reproducible manner, the device of FIG. 4 includes an indicator ring 55 that fits inside the upper portion 46 of the stretcher component. FIG. 5 is a top view of the indicator ring 55 and the inwardly directed flange 53 of the cap 52. The indicator ring 55 is marked with indicia 61 to show the degree of rotation of the cap, and the inwardly directed flange 53 is marked 62 as well. The arrow 63 shows the direction of rotation of the cap and hence the marking 62 on the flange. The location of the marking 52 relating to the indicia 61 on the indicator ring provides a quantitative representation of the degree of stretch imparted to the membrane.

Figure 7:
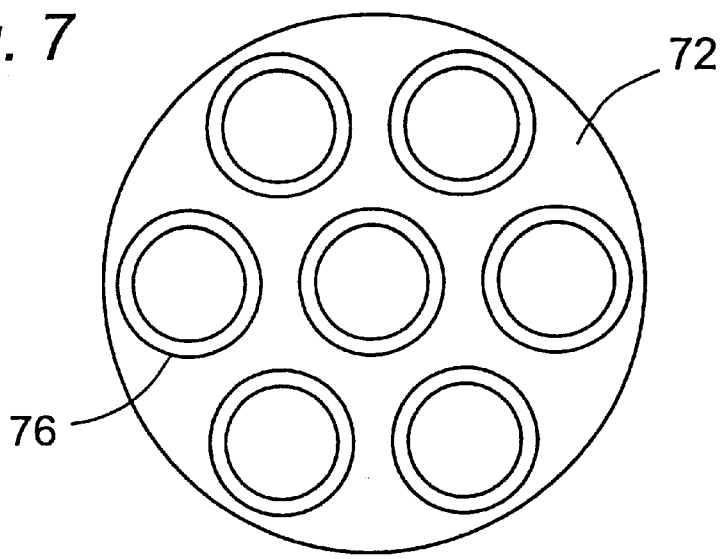
FIG. 7 is a plan view of the stretcher component of the device of FIG. 6.
Figure 8:
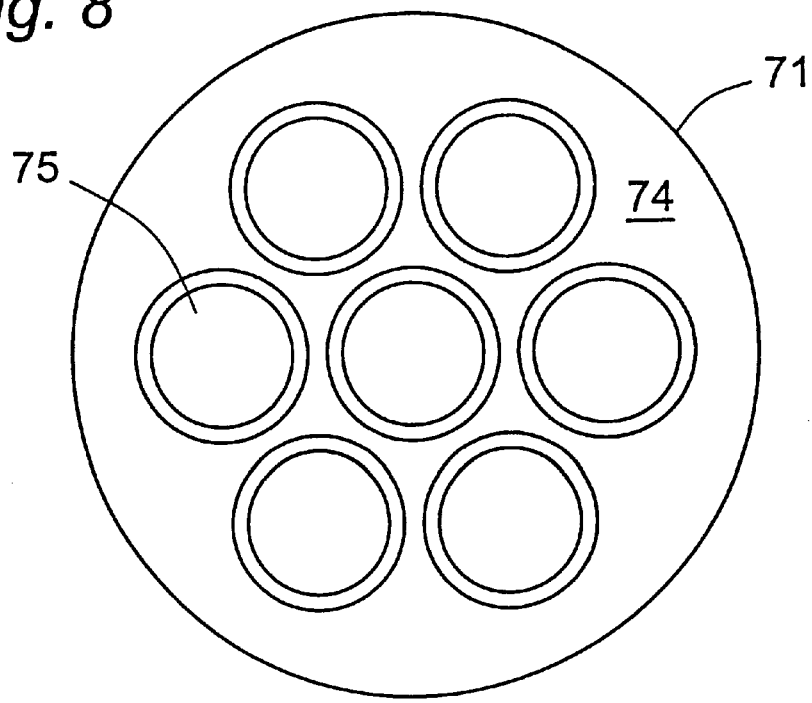
FIG. 8 is a plan view of the membrane support component of the device of FIG. 6.

The multiwell device shown in FIGS. 6, 7, and 8 also consists of three components—a membrane support 71, a stretcher component 72, and an actuator component 73. The membrane support 71 is a hollow cylinder with a plate 74 at one end. The plate 74 contains seven circular openings 75, each one containing a groove (not shown) around its periphery to receive an O-ring, which is held in place by friction to hold individual membranes taut across each opening in the same manner as the O-ring 15 of FIGS. 1 and 2. Examples of suitable O-rings are Viton O-rings (2–113; ASI Manufacturing, San Diego, Calif., USA). The stretcher component 72 is a circular plate into which seven cylinders 76 are formed (machined or molded), each cylinder being circular and hollow and open from top to bottom. The actuator component 73 is similar in construction to the actuator cylinder 16 of FIGS. 1 and 2, and functions in the same manner. Threads 77 on the interior of the actuator component mate with threads 78 on the exterior of the membrane support. The cylinders 76 of the stretcher component fit closely (but without friction) inside the circular openings 75 of the membrane support, and prevent rotation of the stretcher component and the membrane support relative to each other. Rotation of the actuator component 73 controls the position of the stretcher component 72 and the degree of stretch in each of the membranes. A transparent protective lid 79 rests atop the actuator component.

Specifications for examples of both single-well and multiwell stretchers are listed in the table below, in which the values given are in millimeters.

Equibiaxial Stretch Device Specifications

| Component | Inner Diameter | Outer Diameter | Height |
|---|---|---|---|
| Single well: | | | |
| Inner (Stretching) Cylinder | 60.0 | 68.0 | 46.5 |
| Intermediate (Membrane Support) Cylinder | 68.2 | 84.0 | 27.3 |
| Outer (Actuator) Cylinder | | | |
| Flange | 56.0 | | |
| Cylinder | 84.5 | 90.0 | 27.8 |
| Multiwell: | | | |
| Stretcher Component | | | |
| Entire | | 68.3 | 26.5 |
| Individual rings | 9.7 | 11.0 | 12.0 |
| Membrane Support | 68.5 | 84.0 | 22.5 |
| Actuator Component | | | |
| Flange | 56.0 | | |
| Cylinder | 84.5 | 93.4 | 23.2 |

The threaded connections in these examples are single-entry threads, with a pitch of 3.4 mm and a depth of 1.5 mm.

EXAMPLES

In the following examples, the technique described by Villarreal, F. J., et al., *Circ. Res.* 62:711–721 (1988) was used to measure the strain distribution on an elastic membrane by homogeneous finite strain analysis, verifying the homogeneity of biaxial strain and the absence of shear. While Villarreal used this technique on heart tissue, it was later used on elastic membranes (as it is here) by Barbee, K. A., et al., *Ann. Biomed. Eng.* 22: 14–22 (1994). In accordance with this technique, latex fluorescent microspheres (1 micron in diameter) were attached to a collagen-coated membrane as markers of material displacement. Three segment lengths between triangular arrangements of microspheres located 5–20 $\mu$m apart were used to calculate the symmetric two-dimensional Lagrangian strain tensor. The components of this strain tensor are an exact description of the two-dimensional shape change of the membrane at each triangle site and are independent of rotations. Each component of the Lagrangian strain tensor $E_{ij}$ is determined by solving the following two-dimensional equation:

$$ds^2 - dS^2 = 2E_{ij} dX_i dX_j \quad (i,j=c, r) \tag{1}$$

The two-dimensional strains are determined with components along the circumferential (c) and radial (r) axes. dS is the segment length between markers in the undeformed state, ds is the length in the deformed state, and $dX_c$ and $dX_r$ are the two-dimensional components of the segment in the undeformed reference state. The two normal strains, $E_{cc}$ and $E_{rr}$, represent the extension of the membrane in the circumferential and radial directions, respectively, while the shear strain, $E_{cr}$, measures any change in angle between the circumferential and radial axes (e.g., twisting). Therefore, for an ideal equibiaxial strain, $E_{cc}=E_{rr}$, and $E_{cr}=0$.

The Lagrangian strains ($E_{cc}$, $E_{rr}$, and $E_{cr}$) are exact but nonlinear measures of membrane deformation and are related to the linear stretch ratios ($\lambda_c$ and $\lambda_r$) and angle change ($\Delta\Theta$) as follows:

$$\lambda_c = \sqrt{2E_{cc}+1} \quad (2)$$

$$\lambda_r = \sqrt{2E_{rr}+1} \quad (3)$$

$$\sin(\Delta\Theta) = \frac{2E_{cr}}{\sqrt{2E_{cc}+1}\sqrt{2E_{rr}+1}} \quad (4)$$

In Equations (2), (3) and (4), the stretch ratios $\lambda_c$ and $\lambda_r$ are the ratios of the final length to the initial length of line elements in the circumferential and radial directions, respectively, and $\Delta\Theta$ is the change of angle between the two line elements. With the stretch ratios, the convenient and commonly used linear strains, $\epsilon_c$ and $\epsilon_r$ (length change divided by initial length), can be computed according to Equations (5) and (6):

$$\epsilon_c = \lambda_c - 1 \quad (5)$$

$$\epsilon_r = \lambda_r - 1 \quad (6)$$

Fluorescent microspheres (1 μm, yellow-green; Molecular Probes, Eugene, Oreg., USA) were vortexed in 1×PBS (2 μL microsphere stock/mL PBS) and sonicated for 20 minutes (Sonicor Instrument, Copiague, N.Y., USA) before seeding onto the substrate. Epifluorescent images of microspheres on the membrane were obtained using a Nikon Diaphot-TMD inverted microscope (Nikon, Tokyo, Japan) with a X10 phase objective, a charge-coupled device video camera (Cohu, San Diego, Calif., USA), and a X4 photo-eyepiece. Video images were acquired to a microcomputer (Apple Macintosh, Cupertino, Calif., USA) via a 640×480 pixel frame grabber board (Quick Capture, Data Translation, Marlboro, Mass., USA) for digital image processing. Marker coordinates before and after stretch were measured using National Institutes of Health (NIH-1) Image software. Strain components were determined from analyses of markers distributed throughout the area of the membrane.

Figure 9:
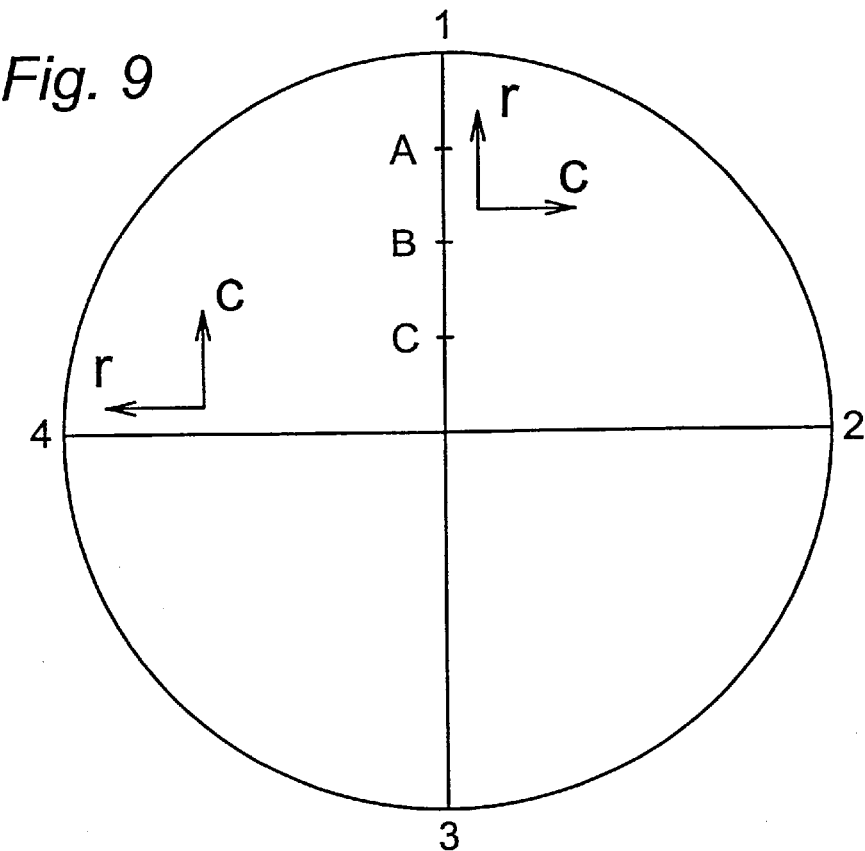
FIG. 9 is a plan view of a membrane to be stretched by the device of FIG. 1, showing axes of reference for the strain components.
Figure 10:
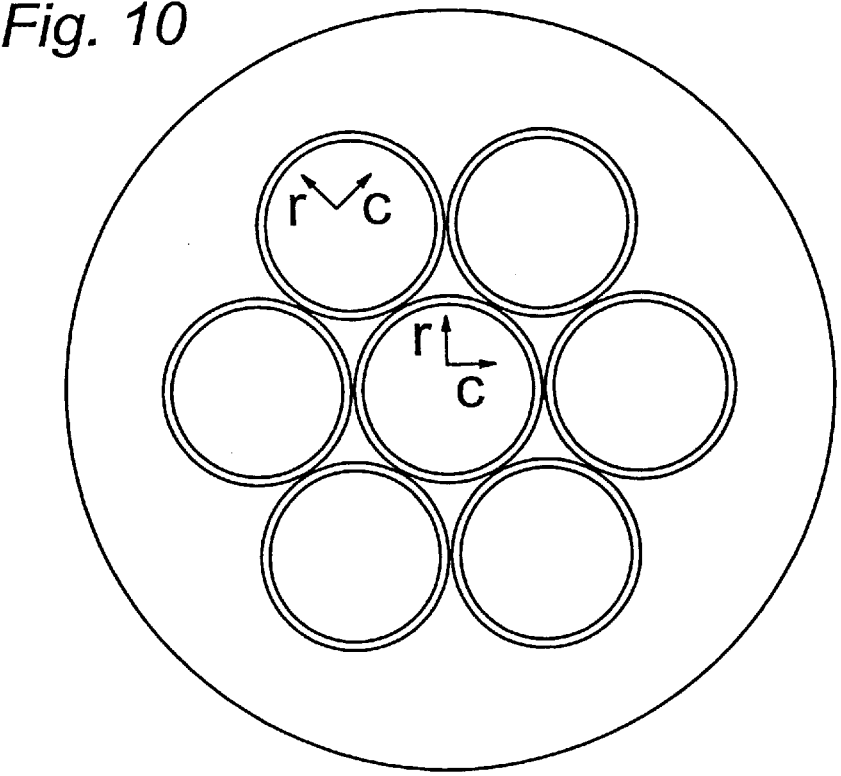
FIG. 10 is a reproduction of FIG. 8, showing axes of reference for the strain components.

FIG. 9 is a schematic of the marker positions used on the elastic membrane for strain analysis in the single-well device. After fluorescent microspheres were seeded onto the collagen-coated substrate, marker triangles were selected at three sites (designated A, B and C) on each of four radii (indicated by the numbers 1, 2, 3 and 4 in the figure). Positions A, B, and C were spaced 11.0 mm apart along each radius, with A located 2.5 mm from the indenter ring and C located 5.5 mm from the center of the well. Two-dimensional strain components were determined from measurements of the displacements of the microspheres, and represented normal strains ($E_{cc}$ and $E_{rr}$) and shear ($E_{cr}$), where c and r represent the circumferential and radial axes, respectively. FIG. 10 is a schematic of the marker positions used for strain analysis in the multiwell device. Two-dimensional strain components were measured at four positions in each of the seven wells for circumferential (c) and radial (r) axes analogous to those of FIG. 9.

Figure 11:
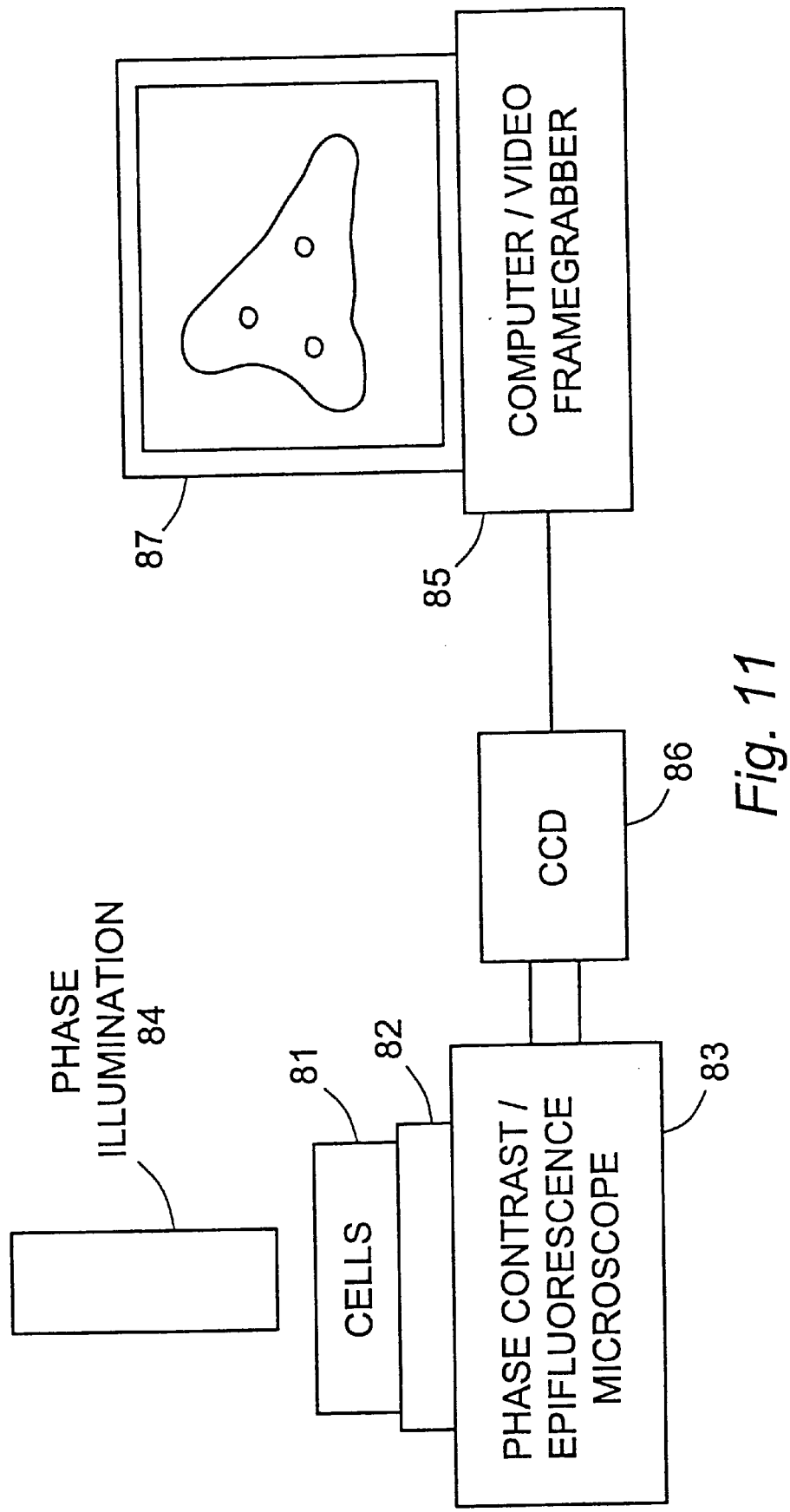
FIG. 11 is a schematic of the experimental apparatus used for the determinations reported in the subsequent figures.

The experimental system used for strain analysis is shown in FIG. 11. Cells 81 were cultured on the substrate 82, and fluorescent microspheres attached to both the substrate and the cells were viewed by phase-contrast and epifluorescence microscopy 83, using phase illumination 84 from above. The image was transferred to a computer 85 via a charge-coupled device 86 camera and a video frame grabber board (in the computer) for image processing and finite strain analysis. Phase-contrast and fluorescence images of the stretched cells were captured in a video monitor 87, permitting visualization of cell borders and identification of the marker triangles on the cells. Two-dimensional strains were determined from measurements of the displacements of the fluorescent markers attached to the substrate or to the apical surface of the cells. Marker triangles were selected from cells and neighboring substrate located within the same view under phase-contrast and fluorescence microscopy. Values of dS, ds, $dX_c$, and $dX_r$ were determined experimentally from the marker positions, and the three strain components ($E_{cc}$, $E_{rr}$, and $E_{cr}$) were calculated in accordance with Equation (1) above. Both the single-well and multiwell devices were calibrated by measuring mean strain as a function of rotation of the actuator component (i.e., the outer cylinder). The reproducibility of the deformation was confirmed by strain analyses in repeated tests.

Cell Culture

Adult rat cardiac fibroblasts were prepared by mincing three to four hearts from 7- to 8-week-old male Sprague-Dawley rats (200–250 g) and enzymatically digesting the minced hearts in a solution containing collagenase (100 Mandl units/mL) and pancreatin (0.6 mg/mL). Pooled cell suspensions were centrifuged, resuspended in Dulbecco's modified Eagle's medium (DMEM; GIBCO BRL, Grand Island, N.Y., USA) with antibiotics (penicillin, streptomycin, and fungizone (PSF); GIBCO, Life Technologies, Inc., Grand Island, N.Y., USA) and 10% fetal bovine serum (FBS), and then plated onto uncoated cell culture dishes for 30 minutes for preferential attachment of fibroblasts. Cardiac fibroblasts were plated at subconfluence onto the elastic membrane substrate of the stretch devices in DMEM/PSF with 10% FBS and then growth-arrested for 24 hours in DMEM/PSF and 0.5% heat-inactivated FBS before stretching.

Verification of Transmission of Strain From Substrate to Cells

To determine how deformation of the membrane related to cell deformation, fluorescent microspheres were attached to both substrate and cultured fibroblasts in a single preparation for strain analysis. Before plating, cell suspensions were washed in PBS and then resuspended in the microspheres/PBS mixture. After a 10-minute incubation, cells were plated to the stretch devices in DMEM/PSF with 10% FBS. Excess microspheres were removed by washing cultures with PBS.

Statistics

Results are expressed as means±standard deviation (SD). Analysis of variance was used for comparisons between groups. Differences were regarded as statistically significant when $P<0.05$. Each experiment was performed independently a minimum of three times.

EXAMPLE 1

This example demonstrates the manner in which circumferential and radial strains vary with the rotation of the actuator cylinder in the single-well device of FIGS. 1 and 2 (with the specifications listed for the single-well device in the above table), as well as the effect of these strains on the mean shear.

Figure 12:
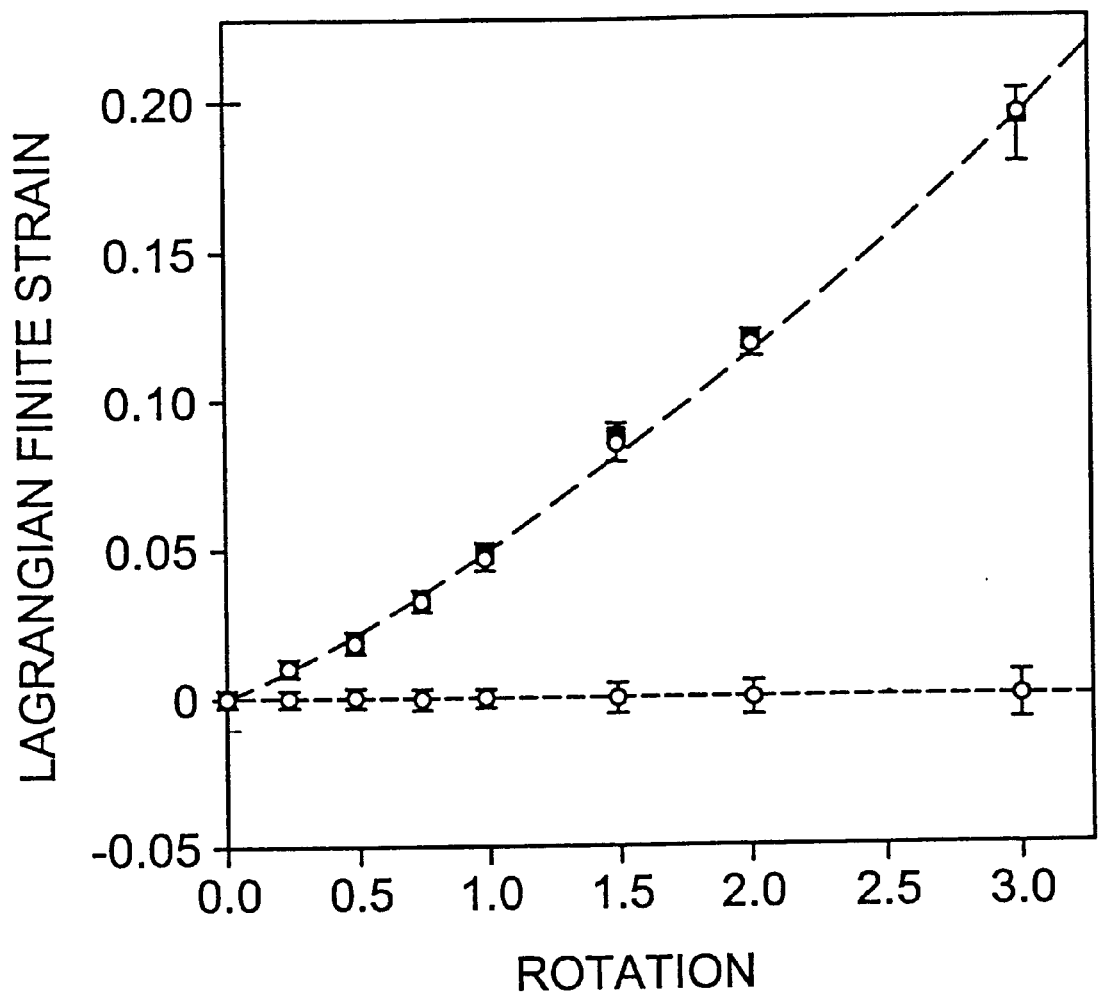
FIG. 12 is a calibration curve for a single-well equibiaxial stretch device in accordance with the present invention.
Figure 13:
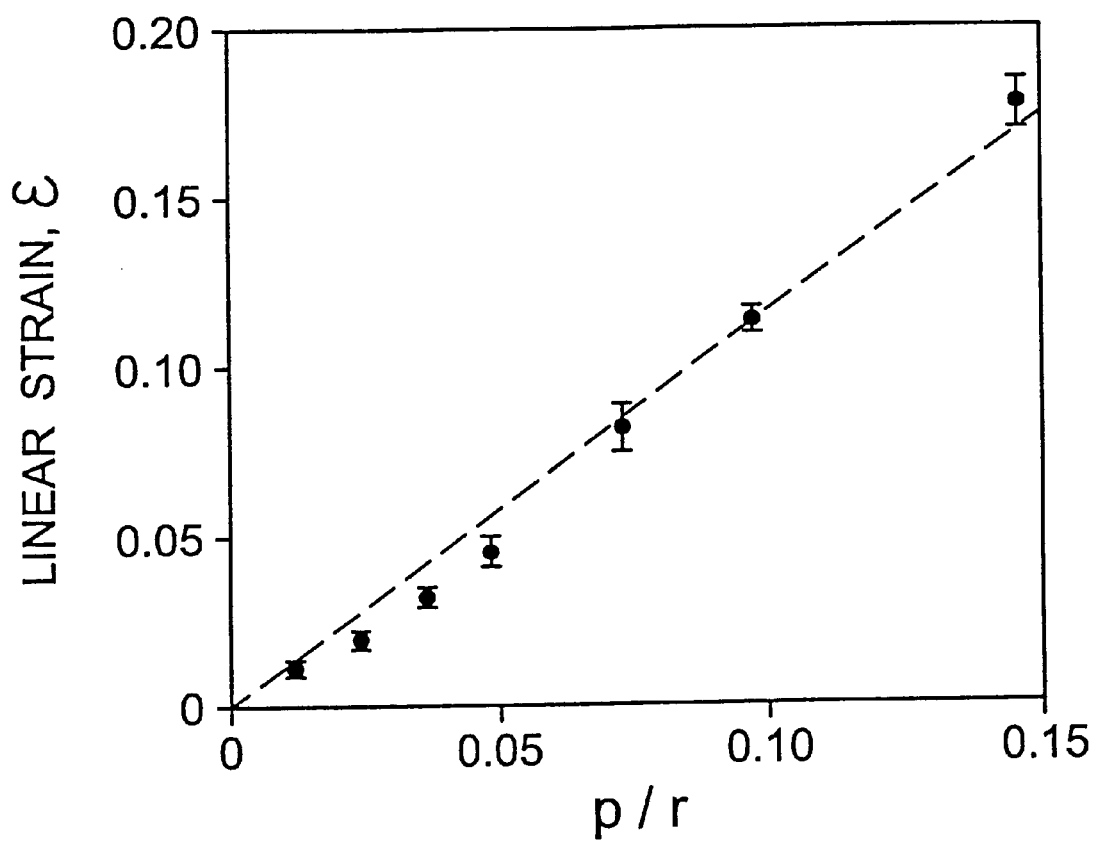
FIG. 13 is a plot of linear strain exerted on the membrane vs. pitch-to-radius ratio of the threads for the single-well device.

Two-dimensional strain distributions were computed for a series of rotations (one rotation=360°) of the actuator cylinder (element 13 in FIG. 1). The device was subjected to 0.25, 0.5, 0.75, 1.0, 1.5, 2.0, and 3.0 rotations. FIG. 12 shows the normal Lagrangian strains ($E_{cc}$ represented by open diamonds and $E_{rr}$ by filled squares) and shear ($E_{cr}$ represented by open circles) determined from the displacements of the fluorescent markers on the membrane at each rotation. FIG. 13 shows the linear strain ($\epsilon$) as a linear function of the pitch-to-radius ratio (p/r) of the device. The linear strain $\epsilon$ was determined from measured equibiaxial strain by Equations (2) through (6). The radius r is the radius of the clamped membrane and the pitch p represents the vertical displacement of the stretcher cylinder (element 11 of FIG. 1) for one full rotation of the actuator cylinder (element 13 of FIG. 1).

FIG. 12 shows that for different rotations of the actuator cylinder (0.25, 0.5, 0.75, 1.0, 1.5, 2.0, and 3.0 rotations), the mean circumferential strain ($E_{cc}$, open diamonds) was not significantly different from the mean radial strain ($E_{rr}$, filled squares), both falling along the rising upper curve, and the mean shear ($E_{cr}$, open circles on the flat lower line) was negligible. For example, for a 0.75 rotation of the device, representative mean strains were $E_{cc}$=0.032±0.003, $E_{rr}$=0.035±0.003, and $E_{cr}$=0.000±0.003 (n=12). A general relationship was determined between linear strain $\epsilon$ in the membrane, the radius r of the clamped membrane, and the vertical displacement of the stretcher cylinder for a given rotation, represented by the pitch p (for one full rotation) of the thread. The linear strain E was calculated from the measured equibiaxial strain by Equations (2) through (6). A no-intercept linear curve fit, shown in FIG. 12, yielded the following relationship between $\epsilon$ and the pitch-to-radius ratio (p/r) of the device:

$$\epsilon = 1.160(p/r), \text{ with } r=0.993$$

The slope of 1.160 was close to unity, as expected.

EXAMPLE 2

This example shows the variation of the two-dimensional strains with the radial or circumferential positions of the marker triangles on the membrane. The single-well device of FIGS. 1 and 2 was again used.

Figure 14:
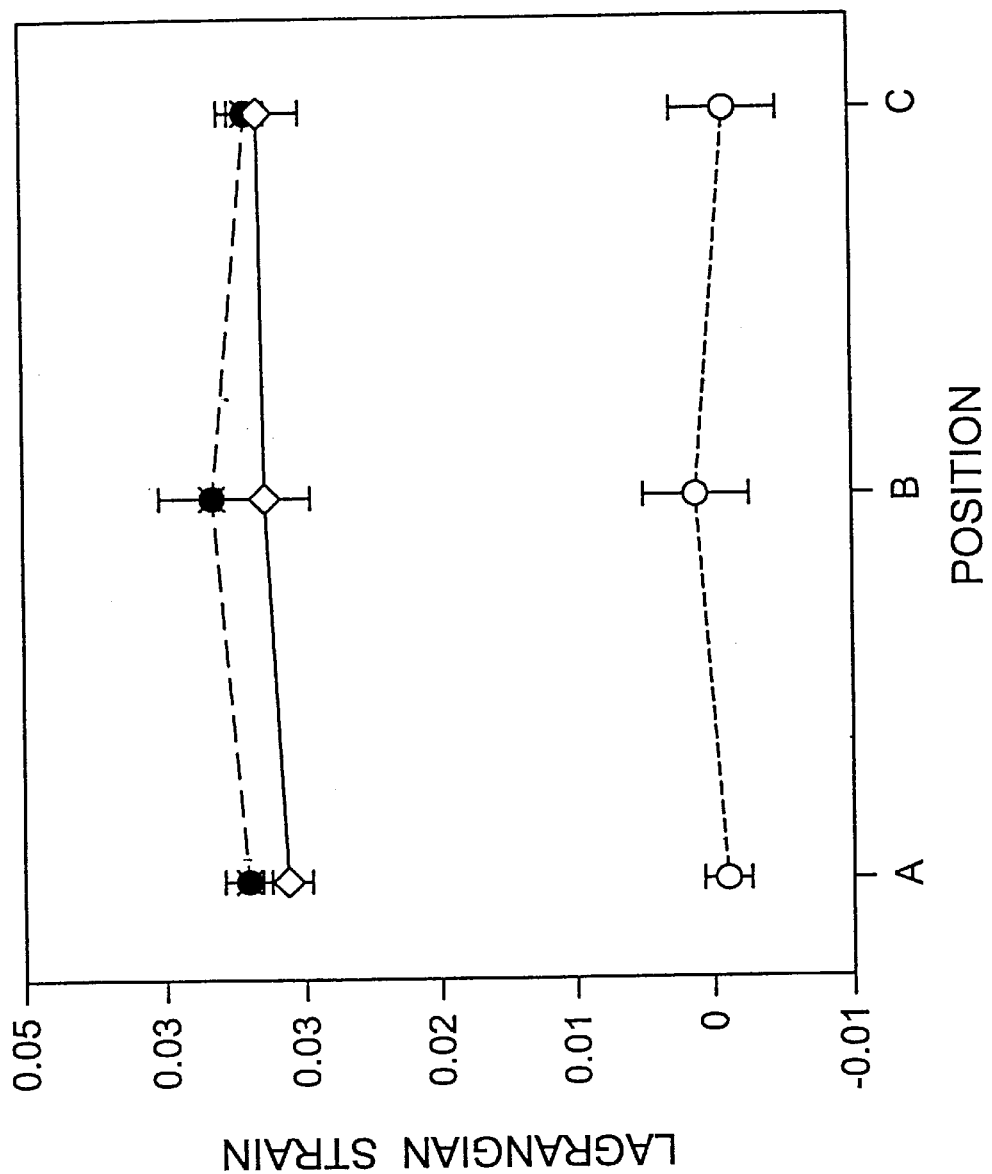
FIG. 14 is a plot showing circumferential strain, radial strain and shear in a membrane stretched on the single-well device as a function of radial position, at radial positions A, B, and C of FIG. 9.
Figure 15:
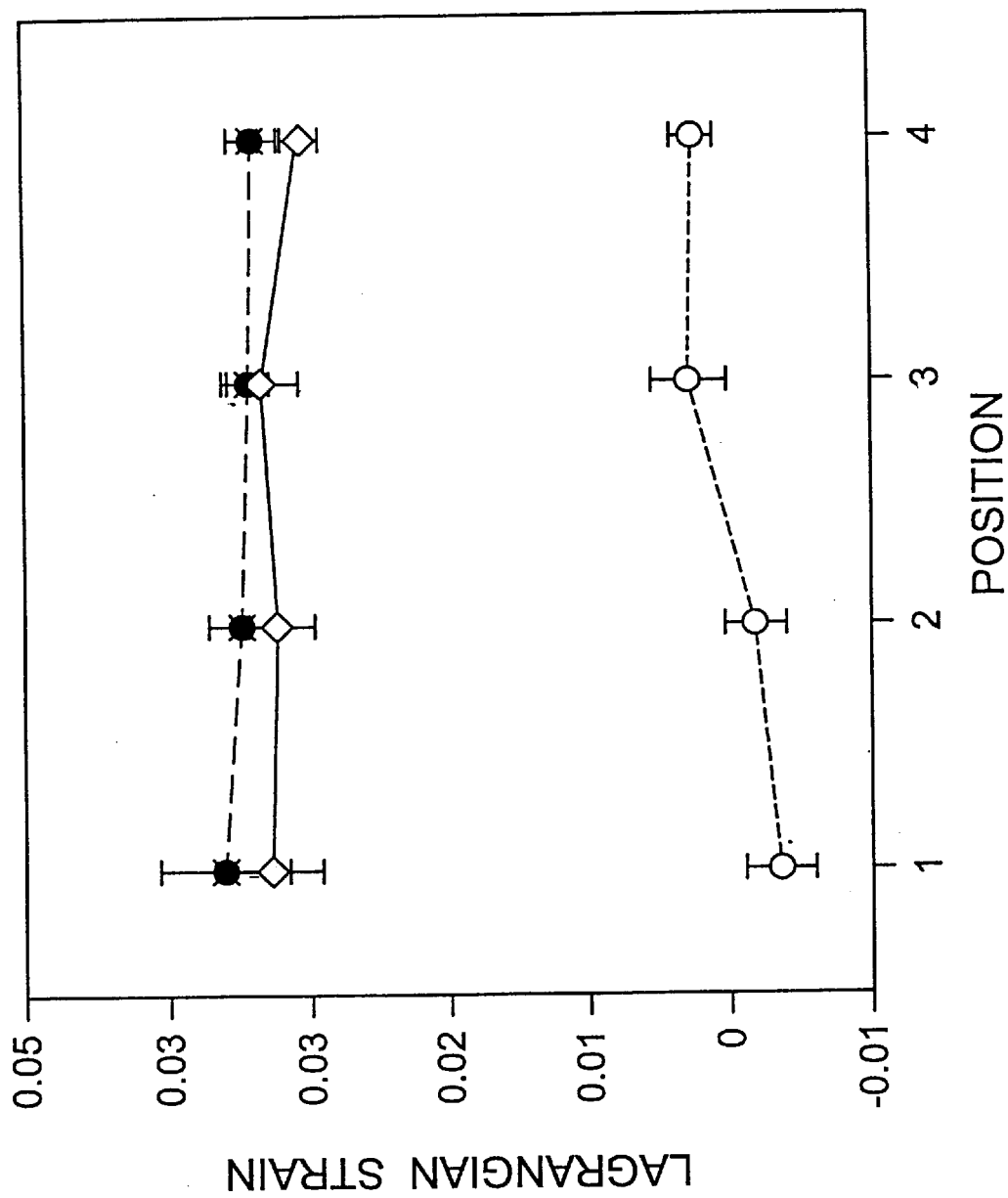
FIG. 15 is a plot showing circumferential strain, radial strain and shear in a membrane stretched on the single-well device as a function of angular (circumferential) position, at angular positions 1, 2, 3, and 4 of FIG. 9.

In FIGS. 14 and 15, two-dimensional strain components are shown as functions of the marker positions on the membrane. Mean normal strains ($E_{cc}$, represented by open diamonds, and $E_{rr}$, represented by filled squares) and shear strain ($E_{cr}$, represented by open circles) were determined for a 0.75 rotation of the screw top in the single-well device. The magnitude of the strain was determined for positions A, B and C along each of the four radii 1, 2, 3 and 4, as indicated in FIG. 9. FIG. 14 shows the strain as a function of the radial position, and FIG. 15 shows the strain as a function of the angular orientation of the radius. FIGS. 14 and 15 show that the mean circumferential strain ($E_{cc}$) was not significantly different from mean radial strain ($E_{rr}$), and that the mean shear ($E_{cr}$) was not significantly different from its value at zero strain.

EXAMPLE 3

This example represents a study similar to that of Example 2, but performed on the multiwell device of FIG. 3.

Figure 16:
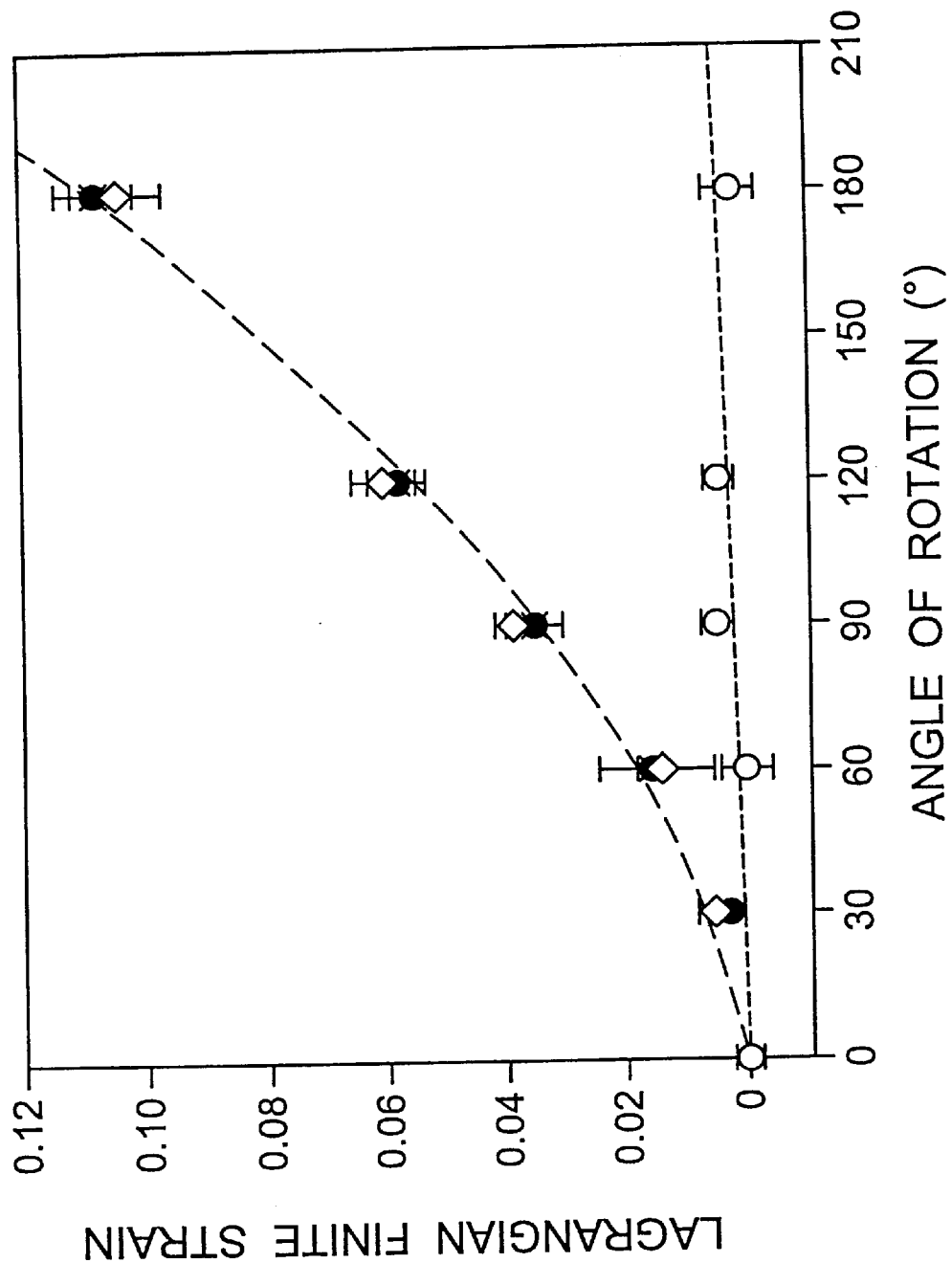
FIG. 16 is a calibration curve for a multiwell equibiaxial stretch device in accordance with the present invention.

The calibration of the multiwell device by the rotation angle of the actuator cylinder (element 33 in FIG. 3) is shown in FIG. 16. To perform the calibration, marker triangles were selected at four positions in each well of the device. The mean normal strains ($E_{cc}$ represented by open diamonds and $E_{rr}$ represented by filled squares) and shear strain ($E_{cr}$ represented by open circles) for the substrate were computed for a series of rotation angles ranging between 0 and 180°.

As shown in FIG. 16, for a 180° angle of rotation, $E_{cc}$=0.104±0.007, $E_{rr}$=0.108±0.006, and $E_{cr}$=0.002±0.004 (n=3). For each angle of rotation in the multiwell stretcher, mean $E_{cc}$ and mean $E_{rr}$ were not significantly different, and the shear $E_{cr}$ was not significantly different from that shown at zero strain.

EXAMPLE 4

This example illustrates the strains imposed on fibroblast cells that are stretched in the single-well device of FIGS. 1 and 2.

Fluorescent latex microspheres were attached to cultured adult rat cardiac fibroblasts, and phase-contrast and epifluorescence images were taken of the fibroblasts. The fluorescent markers and cell outlines were both visualized in these representative images, permitting the use of markers that were spaced 5–20 $\mu$m apart and located within the cell borders. Displacements of marker triangles were measured to determine mean values of all three types of strains ($E_{cc}$, $E_{rr}$, and $E_{cr}$) that the cells were subjected to as the substrate was stretched in the single-well device. The displacements of markers on both the substrate and the cultured fibroblasts, which were located within the same field of view, were measured for three nominal strains (3, 6, and 10%, i.e., 0.03, 0.06, and 0.10, respectively).

Figure 17:
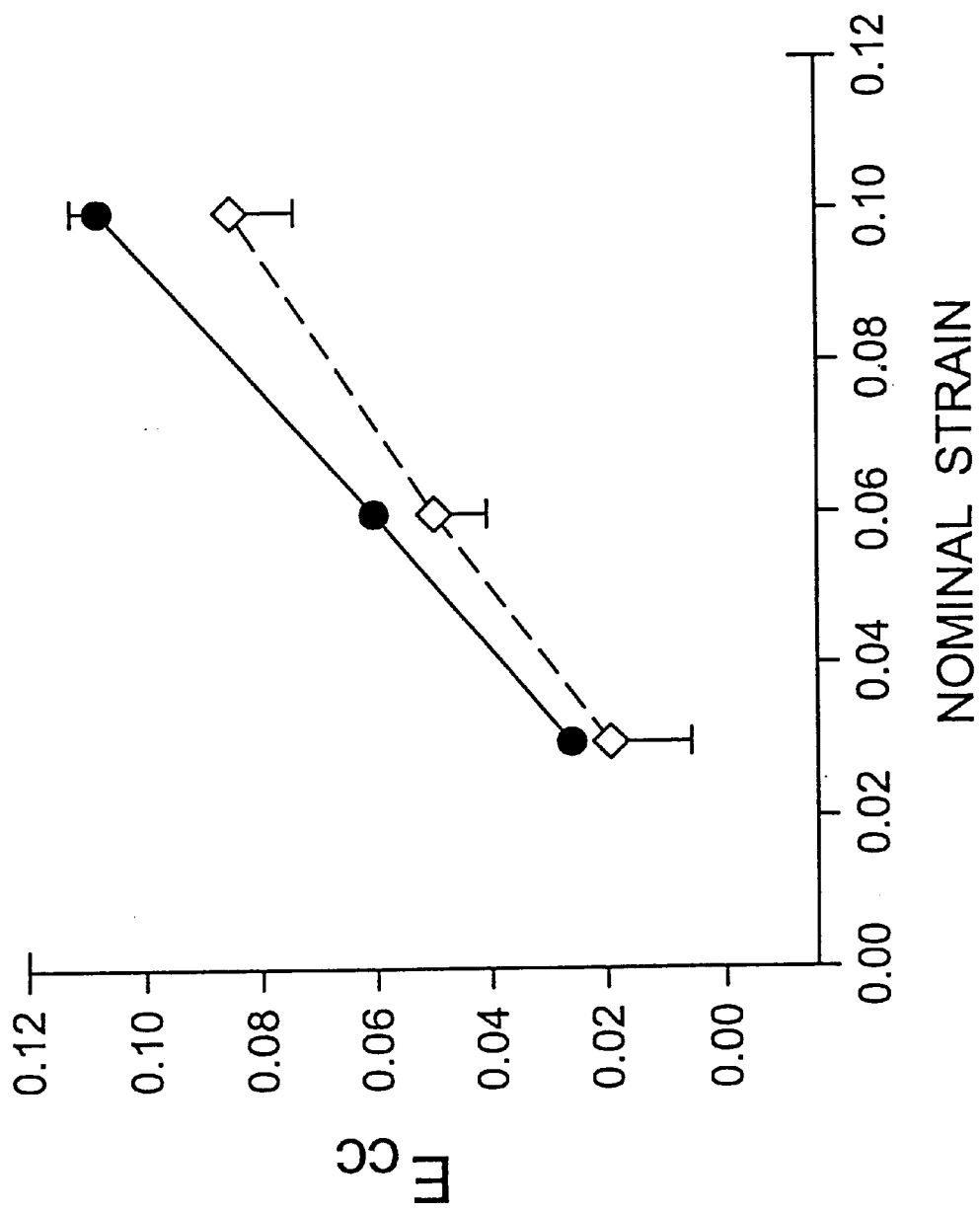
FIG. 17 is a plot of measured (actual) circumferential strain vs. nominal strain for the membrane (closed circles) and for the cells (open diamonds) on the single-well device.
Figure 18:
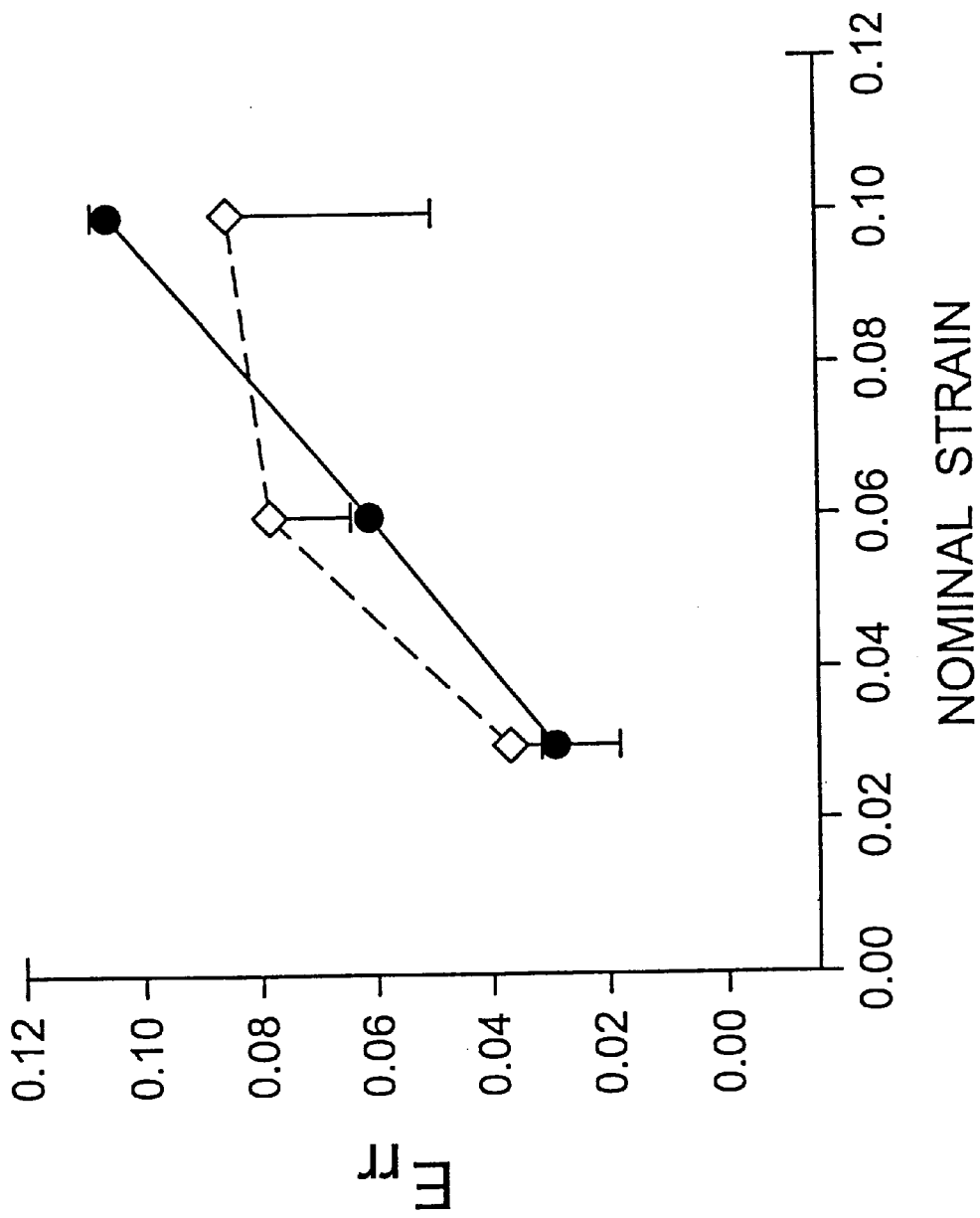
FIG. 18 is a plot of measured (actual) radial strain vs. nominal strain for the membrane (closed circles) and for the cells (open diamonds) on the single-well device.
Figure 19:
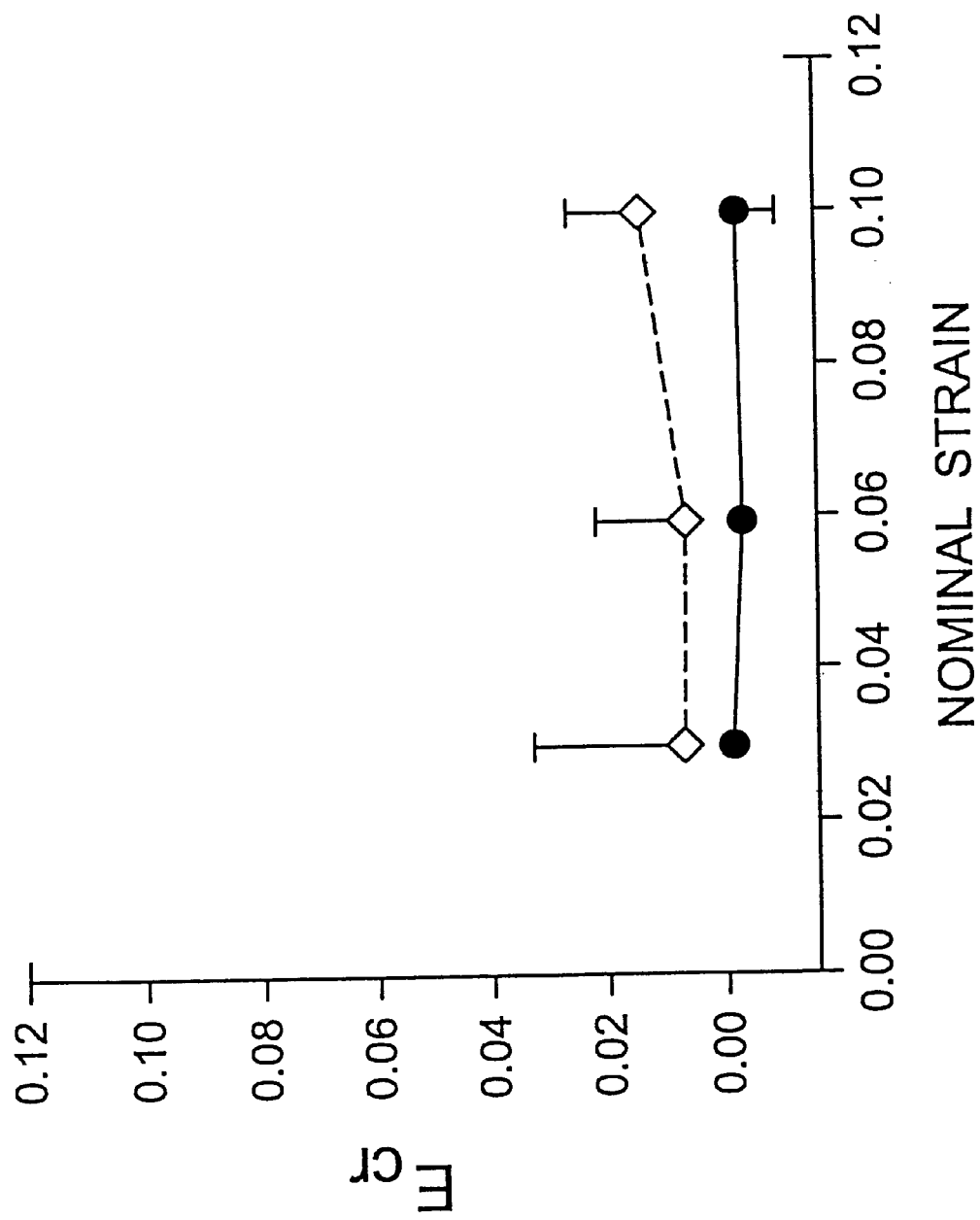
FIG. 19 is a plot of measured (actual) shear vs. nominal strain for the membrane (closed circles) and for the cells (open diamonds) on the single-well device.

The results are plotted in FIGS. 17, 18, and 19, representing $E_{cc}$, $E_{rr}$, and $E_{cr}$, respectively, for the substrate (filled circles) and the cells (open diamonds). These plots quantitatively show how closely the cell strains match the substrate strains. Similar to the calibration results for the device (presented in Example 2), the mean $E_{cc}$ and $E_{rr}$ strains for the substrate were not significantly different and the mean $E_{cr}$ for the substrate was negligible, within 0.5–1.0% measurement error. Comparing the strain values for the substrate with those for the cells, the mean cell strain components were not significantly different from those of the substrate strains for each nominal strain, except for $E_{cc}$ at 10% nominal strain, where mean cell $E_{cc}$=0.084±0.011 compared with mean substrate $E_{cc}$=0.107±0.004 (n=4; P<0.05). Measurement errors for cell strains at each nominal strain were larger than the errors for substrate strain analysis, ranging between 0.9 and 3.5%.

The devices of the present invention can be made from conventional materials of construction (of which polycarbonate is a convenient example), preferably those that are easily machined or injection molded. Various components of the devices can be made to be disposable, if desired. Materials can also be selected that are biocompatible and readily sterilized by autoclave or ultraviolet exposure. The devices shown in the Figures are simple to assemble and do not require the use of glues or any other adhesives or elements for fastening or securing the parts together. In the single-well version, a pin inserted between the two non-rotating cylinders (in complementary facing grooves) or a protruding ridge in one cylinder and a complementary groove in the other are sufficient to prevent twisting of the membrane. Alternative means for preventing relative rotation of these components will be readily apparent to anyone familiar with the construction of simple mechanical devices.

The devices are useful for the study of a wide variety of cells and cell types, including the adult rat cardiac fibroblasts used in the examples above as well as neonatal rat cardiac myocytes, human ligament fibroblasts, and various established cell lines (e.g., NIH/3T3, HT-1080, CHO-K1). The larger plating area of the single-well device can also be used in applications such as RNA and DNA isolation, immunoprecipitation, protein purification, or Western blotting. The reduced cell culture area in the multiwell version permits experiments requiring conservation of reagents such as expensive antibodies or radioactive substances, e.g., [$^3$H]thymidine used in proliferation assays. The separate culture wells in the multiwell version are also useful for studies requiring multiple treatments within a single controlled system. For example, individual membranes within one multiwell device may be coated with different extracellular matrix proteins, such as fibronectin or vitronectin, to examine the potential matrix-dependent responses of cells to mechanical strain.

Both the single-well and multiwell stretchers permit in situ visualization of cell geometry, function, and deformation by using an elastic membrane that is transparent and accessible to the objective of an inverted microscope. In addition, the fact that the device holds the membrane in a planar configuration in a fixed plane during the deformation allows one to visualize the stretched substrate or cells at any location. Calibration of the device permits one to apply homogeneous and planar biaxial strain in a reproducible manner by rotation of the actuator component.

Since the two-dimensional strains remain biaxial with strains along the two orthogonal axes being in a constant proportion (whether equibiaxial or otherwise), and planar as the load on the membrane is both increased and decreased, both the single-well and multiwell devices can also be used to apply a compressive (negative) equibiaxial strain to cultured cells. This is done by plating the cells onto the membrane while the membrane is stretched, then partially relaxing the stretch to an accurately controlled degree by rotating the actuator component in the opposite direction.

The device will most often be used in the orientation shown in the drawings, i.e., with the membrane beneath both the membrane support cylinder and the stretcher cylinder, and the cells cultured on the interior surface of the membrane, i.e., the surface on the same side as the stretcher cylinder. The device can also be used in an inverted orientation, membrane above both the support cylinder and the stretcher cylinder, and the cells cultured on the exterior surface of the membrane. Likewise, observation can be performed either from the bottom of the membrane or from the top. Other uses will be readily apparent to those skilled in the art. For example, the membrane can be placed above a culture dish and thereby define one boundary of an space defined by the membrane and a culture dish. The space can be filled with cell growth medium and the cells grown in it. Also, cells such as neurons can be seeded on cover slips and these held on the membrane by surface tension.

The degree of transmission of strain from the substrate membrane to cells cultured on the membrane may vary with cell type. Barbee, K., et al., *Ann. Biomed. Eng.* 22:14–22 (1994) report differences in cell and substrate strains in biaxially stretched vascular smooth muscle cells. Ingber, D. E., et al., *J. Biomech.* 28:1471–1484 (1995) report that inhomogeneities in cell strains, and therefore cell shape, may depend on the polarity, adhesion properties, or cytoskeletal structure in cells. In particular, deformation of the cytoskeleton may be an important mechanism of force transmission and signal transduction within a cell (Davies, P. F., *Physiol. Rev.* 75:519–560 (1995)).

Although stress or strain has been shown to be a major determinant in the regulation of cellular function in tissues such as skin, blood vessels, and the heart, in vivo deformation of these tissues may be complex. Therefore, it may be important to determine whether mechanical regulation of cell function depends on different magnitudes and patterns of cell strain. For example, stretch-induced cellular responses may depend not only on cell strain magnitude along a defied axis but on specific mechanical parameters such as tensile (positive) or compressive (negative) strains, shear strains, or area changes. The dependence of cell function on such strain parameters may be inferred from equibiaxial strain data, especially when combined with results from uniaxial cell stretch. Furthermore, while the full relationship between two-dimensional mechanical stretch and cellular responses may not be deduced from equibiaxial data alone, additional biaxial data may be obtained if the equibiaxial device is modified to prescribe nonequibiaxial strains. Such strains can be achieved by the use of an elliptical attachment to the stretcher cylinder to deform the clamped membrane. The resulting biaxial deformation will be determined by the major and minor axes of the ellipse. By varying different elliptical attachments, one can prescribe different states of homogeneous biaxial stretch in the membrane.

As an option, the devices of this invention can be supplemented with a motor or pump and a linear or rotary drive mechanism to provide cyclic vertical displacement to the stretcher cylinder(s). Although fluid movement is negligible during the static application of strain in the use of this device, the minimization of fluid flow is a preferred consideration, to reduce the potential effects of fluid shear stress on cell function. The device can be placed inside an incubator, preferably one that allows in situ visualization to permit the quantification of cell strain during mechanical loading.

In addition to the embodiments that are described in detail above, this invention encompasses numerous variations that will be readily apparent to those familiar with cell stretching procedures. For example, several different extracellular matrix materials that are known by cell biologists to be useful for particular purposes can be applied as coatings for the membrane. These coatings can be applied either uniformly or directionally to the membrane. As another example, the lid covering the top of the device (item 9 in FIG. 1 or item 79 in FIG. 6) can be removable and/or openable (without being removed) to permit access to the cells for micromanipulation with microelectrodes, microcapillaries, or micromanipulators. As a further example, the device can provide access from the bottom for inverted microscopes, such as Kohler, Nomarski, fluorescent and confocal microscopes, as well as multi-photon optics. Still further, fluid shear measurements can be taken by mounting a plate over the membrane to create a chamber through which nutrient medium can be pumped. This permits studies of the effect of the resulting shear force on cell attachment to the membrane, and also permits the quantification of the resistance of the cells to this force.

Most experimental approaches toward the study of mechanical stretch and cellular function have not properly defined and quantified the states of cellular deformation. The simple and practical experimental system which is the subject of this invention allows for the reproducible application and quantification of homogeneous equibiaxial strain in cultured cells, thereby providing a systematic and quantitative method for correlating external mechanical stimuli to cellular and molecular mechanisms of mechanotransduction.

What is claimed is:

1. Apparatus for imparting biaxial strain to biological cells adhering to an elastic membrane, said apparatus comprising:

a membrane support having a tubular passageway with an opening at one end and means for affixing such a membrane across said opening;

a cylinder, open and hollow, terminating at one end in a planar rim, said cylinder disposed inside said tubular passageway, such that said membrane support and said cylinder are on the same side of any such membrane affixed across said opening; and actuating means coupled to said membrane support through a threaded connection and engaging said cylinder, whereby rotation of said actuating means along said threaded connection causes said cylinder to move longitudinally within said tubular passageway such that said planar rim protrudes through said opening to a degree corresponding to the degree of rotation and engages any such membrane affixed across said opening, thereby biaxially stretching a central portion of said membrane in a planar configuration across said planar rim.

2. Apparatus in accordance with claim 1 further comprising means for limiting movement of said cylinder to a longitudinal direction relative to said tubular passageway.

3. Apparatus in accordance with claim 1 in which said cylinder is defined as a first cylinder, said membrane support is a second cylinder, and said actuating means is a third cylinder encircling said second cylinder, and said threaded connection comprises threads on an internal surface of said third cylinder mated with threads on an external surface of said second cylinder.

4. Apparatus in accordance with claim 3 in which said third cylinder has a flange extending across said second cylinder to contact said first cylinder.

5. Apparatus in accordance with claim 3 further comprising a transparent protective lid sized and shaped to rest atop said first, second and third cylinders.

6. Apparatus in accordance with claim 1 in which said tubular passageway and said planar rim have circular cross sections, thereby imparting equibiaxial strain to said biological cells.

7. Apparatus in accordance with claim 1 in which said planar rim has an elliptical cross section.

8. Apparatus in accordance with claim 1 further comprising a stand to support said membrane support, cylinder and actuating means such that any such membrane affixed across said opening forms the lowermost plane of said membrane support, cylinder and actuating means, and such that said membrane remains at a fixed position relative to said stand regardless of the degree of stretching of said membrane by said cylinder.

9. Apparatus in accordance with claim 1 in which said means for affixing such a membrane comprises a snap ring defined as a rigid ring with a protruding axial rim and a channel in said membrane support surrounding said opening, said channel sized to receive said protruding axial rim in a friction fit.

10. Apparatus in accordance with claim 1 further comprising a ring bearing indicia that indicate relative angular positions, which together with indicia on said actuating means provides a reproducible indication of the degree of rotation of said actuating means and hence the degree of stretch imparted to said membrane.

11. Apparatus for imparting equibiaxial strain to biological cells adhering to a plurality of elastic membranes, said apparatus comprising:

a membrane support having a plurality of tubular passageways each with an opening at one end, and means for affixing such membranes thereto with one such membrane across each of said openings;

a membrane stretching member comprising a plurality of cylinders, open and hollow, equal in number to said tubular passageways and arranged in an array complementary to said tubular passageways, each cylinder terminating at one end in a planar rim; and actuating means coupled to said membrane support through a threaded connection and engaging said membrane stretching member, whereby rotation of said actuating means along said threaded connection causes said cylinders to move longitudinally within said tubular passageways such that said planar rims protrude through said openings to a degree corresponding to the degree of rotation and engage any such membranes affixed across said openings, thereby equibiaxially stretching a central portion of each of said membranes in a planar configuration across said planar rims.

12. Apparatus in accordance with claim 11 further comprising a stand to support said membrane support, membrane stretching member and actuating means such that any such membranes affixed across said openings form the lowermost plane of said membrane support, cylinder and actuating means, and such that said membranes remain at a fixed position relative to said stand regardless of the degree of stretching of said membranes by said cylinders.

13. Apparatus in accordance with claim 11 in which said membrane support has a cylindrical outer surface and said actuating means is a member having a cylindrical inner surface, and said threaded connection comprises threads on said cylindrical outer surface mated with threads on said cylindrical inner surface.

14. Apparatus in accordance with claim 11 further comprising a transparent protective lid sized and shaped to rest atop said membrane support, membrane stretching member and actuating means.

* * * * *